(12) United States Patent
Peterson et al.

(10) Patent No.: US 11,827,600 B2
(45) Date of Patent: Nov. 28, 2023

(54) CRYSTALLINE FORMS OF TROFINETIDE

(71) Applicant: Acadia Pharmaceuticals Inc., San Diego, CA (US)

(72) Inventors: Matthew Peterson, San Diego, CA (US); Marlon Carlos, Glendale, AZ (US); Martin Bernard Catherine Bousmanne, Woluwe Saint-Lambert (BE); Cecilia Betti, Brussels (BE); David T. Jonaitis, Brookston, IN (US); Lisa M. McCracken, Lafayette, IN (US); Lisa M. Grove, Lafayette, IN (US)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 17/862,865

(22) Filed: Jul. 12, 2022

(65) Prior Publication Data

US 2023/0023114 A1 Jan. 26, 2023

Related U.S. Application Data

(60) Provisional application No. 63/220,660, filed on Jul. 12, 2021.

(51) Int. Cl.
*C07D 207/16* (2006.01)

(52) U.S. Cl.
CPC ........ *C07D 207/16* (2013.01); *C07B 2200/13* (2013.01)

(58) Field of Classification Search
CPC .................................................. C07B 2200/13
See application file for complete search history.

(56) References Cited

U.S. PATENT DOCUMENTS

| 7,041,314 | B2 | 5/2006 | Abood et al. |
| 7,605,177 | B2 | 10/2009 | Gluckman et al. |
| 7,714,020 | B2 | 5/2010 | Gluckman et al. |
| 7,863,304 | B2 | 1/2011 | Brimble et al. |
| 7,887,839 | B2 | 2/2011 | Wen et al. |
| 8,178,125 | B2 | 5/2012 | Wen et al. |
| 8,496,963 | B2 | 7/2013 | Wen et al. |
| 8,546,530 | B2 | 10/2013 | Cellens et al. |
| 8,637,567 | B2 | 1/2014 | Gluckman et al. |
| 9,212,204 | B2 | 12/2015 | Glass et al. |
| 9,708,366 | B2 | 7/2017 | Glass et al. |
| 9,790,264 | B2 | 10/2017 | Lee et al. |
| 10,143,626 | B2 | 12/2018 | Li |
| 10,258,575 | B2 | 4/2019 | Li |
| 10,363,220 | B2 | 7/2019 | Li |
| 10,973,767 | B2 | 4/2021 | Li |
| 11,278,499 | B2 | 3/2022 | Li |
| 11,370,755 | B2 | 6/2022 | Blower et al. |
| 2009/0074865 | A1 | 3/2009 | Wen et al. |
| 2014/0147491 | A1 | 5/2014 | Glass et al. |
| 2020/0093848 | A1 | 3/2020 | Poe et al. |

FOREIGN PATENT DOCUMENTS

| WO | WO-2021026066 A1 | 2/2021 |
| WO | WO-2021086892 A1 | 5/2021 |

OTHER PUBLICATIONS

Cacciatore, I., et al., "Development of glycine-α-methyl-proline-containing tripeptides with neuroprotective properties," *European Journal of Medicinal Chemistry* 108:553-563, Elsevier, Netherlands (Jan. 2016).
Harris, P., et al., "Synthesis of proline-modified analogues of the neuroprotective agent glycyl-1-prolyl-glutamic acid (GPE)," *Tetrahedron* 61:10018-10035, Elsevier, Netherlands (Oct. 2005).
International Search Report for International Application No. PCT/US2022/036768, dated Oct. 5, 2022, International Searching Authority, United States, 3 pages.

*Primary Examiner* — Jeffrey S Lundgren
*Assistant Examiner* — Eric Tran
(74) *Attorney, Agent, or Firm* — Sterne, Kessler, Goldstein & Fox P.L.L.C

(57) ABSTRACT

This disclosure provides crystalline forms of trofinetide and trofinetide hydrate, pharmaceutical compositions comprising crystalline forms of trofinetide and trofinetide hydrate, methods of making crystalline forms of trofinetide or trofinetide hydrate, and methods of treating a disease, condition, or disorder in a subject comprising administering a composition comprising crystalline forms of trofinetide or trofinetide hydrate to the subject.

19 Claims, 12 Drawing Sheets

CRYSTALLINE FORMS OF TROFINETIDE

BACKGROUND OF THE INVENTION

Field of Invention

This disclosure provides crystalline forms of trofinetide and trofinetide hydrate, pharmaceutical compositions comprising crystalline forms of trofinetide and trofinetide hydrate, methods of making crystalline forms of trofinetide or trofinetide hydrate, and methods of treating a disease, condition, or disorder in a subject comprising administering a composition comprising crystalline forms of trofinetide or trofinetide hydrate to the subject.

Background

Glycyl-L-2-methylprolyl-L-glutamic acid (also known as trofinetide) is a synthetic analog of glycine-proline-glutamate (also known as glypromate or GPE). GPE occurs naturally in the brain. It is the N-terminal tripeptide of the insulin-like growth factor 1 (IGF-1) protein.

U.S. Pat. No. 7,041,314 discloses trofinetide, methods of making trofinetide, and methods of using trofinetide to treat a disease, disorder, or condition, e.g., neural degeneration caused by hypoxia-ischemia or toxic injury. U.S. Pat. No. 7,605,177 discloses methods of using trofinetide to treat disease, e.g., neurodegeneration and chronic neurodegenerative disorders, e.g., Alzheimer's disease, Parkinson's disease, Huntington's disease, diabetic neuropathies caused by type I or type II diabetes, autoimmune disorders of the brain, or multiple sclerosis. U.S. Pat. No. 7,714,020 discloses methods of using trofinetide to treat a disease, disorder, or condition, e.g., brain injuries caused by traumatic brain injury, stroke, hypoxia/ischemia and toxic injury. U.S. Pat. No. 7,863,304 discloses methods of using trofinetide to treat a disease, disorder, or condition, e.g., chronic neurodegenerative disorders such as Parkinson's disease. U.S. Pat. No. 8,637,567 discloses methods of using trofinetide to treat a disease, disorder, or condition, e.g., a cognitive disorder or memory disorder. U.S. Pat. Nos. 7,887,839, 8,178,125, and 8,496,963 disclose oral formulations of trofinetide to treat a variety of diseases, disorders, or conditions. U.S. Pat. Nos. 9,708,366 and 9,212,204 disclose methods of using trofinetide to treat a disease, disorder, or condition, e.g., Autism Spectrum Disorders, e.g., autism, autistic disorder Asperger syndrome, childhood disintegrative disorder, pervasive developmental disorder-not otherwise specified (PDD-NOS), Fragile X syndrome, or Rett syndrome.

BRIEF SUMMARY OF THE INVENTION

There exists a need for chemically stable solid forms of trofinetide for use in treating Rett Syndrome, Fragile X Syndrome, traumatic brain injury, and other diseases, disorders, and conditions in a subject.

In one aspect, the present disclosure provides a crystalline polymorphic form of trofinetide or trofinetide hydrate.

In another aspect, the present disclosure provides methods of making a crystalline polymorphic form of trofinetide.

In another aspect, the present disclosure provides compositions comprising a crystalline polymorphic form of trofinetide or trofinetide hydrate, and one or more excipients.

In another aspect, the present disclosure provides a method of making a composition comprising a crystalline polymorphic form of trofinetide or trofinetide hydrate, and one or more excipients.

In another aspect, the present disclosure provides a method of using a crystalline polymorphic form of trofinetide or trofinetide hydrate to treat a disease, disorder, or condition, e.g., traumatic brain injury or a neurodevelopmental disorder, in a subject.

In another aspect, the present disclosure provides a kit comprising a crystalline polymorphic form of trofinetide or trofinetide hydrate.

DETAILED DESCRIPTION OF THE INVENTION

I. Crystalline Trofinetide or Trofinetide Hydrate

Figure 1:
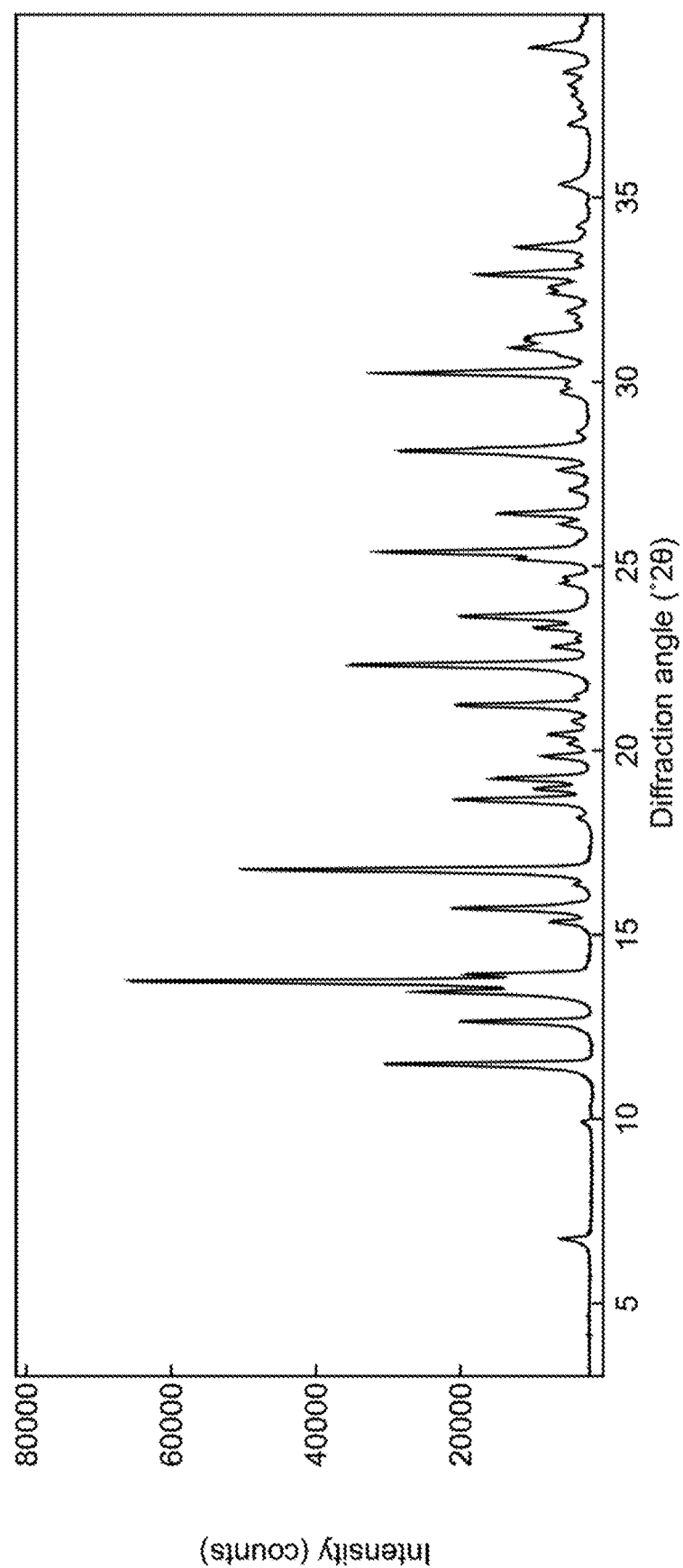
FIG. 1 is a XRPD diffractogram of Form A.

In one embodiment, the present disclosure provides a crystalline polymorphic form of trofinetide or a crystalline polymorphic form of trofinetide hydrate, collectively referred to as a "trofinetide polymorph."

In another embodiment, the trofinetide polymorph is a crystalline trofinetide hydrate represented by the formula: trofinetide.$xH_2O$, wherein x is about 2 to about 4. In another embodiment, the trofinetide polymorph is trofinetide.$xH_2O$, wherein x is about 2.5 to about 3.5. In another embodiment, the trofinetide polymorph is trofinetide.$xH_2O$, wherein x is about 2. In another embodiment, the trofinetide polymorph is trofinetide.$xH_2O$, wherein x is about 2.5. In another embodiment, the trofinetide polymorph is trofinetide.$xH_2O$, wherein x is about 3. In another embodiment, the trofinetide polymorph is trofinetide.$xH_2O$, wherein x is about 3.5. In another embodiment, the trofinetide polymorph is trofinetide.$xH_2O$, wherein x is about 4. These crystalline trofinetide.$xH_2O$ polymorphs are collectively referred to as "Form A".

In another embodiment, Form A is characterized as having a PXRD pattern a powder x-ray diffraction pattern with a peak in the range of 6.6-6.8, a peak in the range of 11.3-11.6, a peak in the range of 12.5-12.7, and a peak in the range of 13.6-13.8 degrees 2Θ using Cu Kα radiation, wherein the 2Θ values are ±0.2 degrees 2Θ; and optionally peaks at 16.8, 22.3, 23.6, 25.3 and/or 28.1 degrees 2Θ±0.2 degrees 2Θ using Cu Kα radiation.

In another embodiment, Form A is characterized as having a PXRD pattern with peaks at 6.7 or 6.8, 11.4 or 11.5, 12.6, and 13.7 or 13.8 degrees 2Θ, and optionally peaks at 16.8, 22.3, 23.6, 25.3 and/or 28.1 degrees 2Θ±0.2 degrees 2Θ using Cu Kα radiation.

In another embodiment, Form A is characterized as having a PXRD pattern with peaks at 6.7, 11.4, 12.6, 13.7, 22.3, 23.6, 25.3 and 28.1 degrees 2Θ using Cu Kα radiation, wherein the 2Θ values are ±0.2 degrees 2Θ.

In another embodiment, Form A is characterized as having a PXRD pattern with peaks at 6.7, 11.4, 12.6, 13.7, 22.3, 23.6, 25.3 and 28.1 degrees 2Θ using Cu Kα radiation.

In another embodiment, Form A is characterized as having a PXRD pattern with peaks at 6.8, 11.5, 12.6, 13.8, and 16.8 degrees 2Θ using Cu Kα radiation, wherein the 2Θ values are ±0.2 degrees 2Θ.

In another embodiment, Form A is characterized as having a PXRD pattern with peaks at 11.5, 12.6, and 13.8 degrees 2Θ using Cu Kα radiation, wherein the 2Θ values are ±0.2 degrees 2Θ.

In another embodiment, Form A is characterized as having a PXRD pattern with peaks at 6.8, 11.5, and 12.6 degrees 2Θ using Cu Kα radiation, wherein the 2Θ values are ±0.2 degrees 2Θ.

In another embodiment, Form A is characterized as having a PXRD pattern with at least three peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least four peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least five peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least six peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least seven peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least eight peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least nine peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with at least ten peaks at 6.8, 9.9, 11.5, 12.6, 13.5, 13.8, 13.9, 15.4, 15.7, 16.3, 16.8, 18.2, 18.7, 19.0, 19.2, 19.8, 20.4, 20.8, 21.2, 21.5, 22.3, 22.8, 23.3, 23.6, 25.4, 26.4, 28.1, 30.2, 32.9, 33.7, 35.4, and/or 39.1 degrees 2Θ using Cu Kα radiation, wherein the 2Θ values are ±0.2 degrees 2Θ.

In another embodiment, Form A is characterized as having a PXRD pattern with peaks at 6.8, 9.9, 11.5, 12.6, 13.5, 13.8, 13.9, 15.4, 15.8, 16.3, 16.8, 18.2, 18.7, 19.0, 19.270, 19.8, 20.4, 20.8, 21.2, 21.5, 22.380, 22.8, 23.3, 23.6, 25.4, 26.4, 28.1, 30.2, 32.9, 33.7, 35.4, and 39.120 degrees 2Θ using Cu Kα radiation, wherein the 2Θ values are ±0.2 degrees 2Θ.

In another embodiment, Form A is characterized as having a PXRD pattern with d-spacings at 13.1, 7.7, 7.0, 6.4, and 5.3 Å using Cu Kα radiation.

In another embodiment, Form A is characterized as having a PXRD pattern with d-spacings at 13.1, 7.7, and 7.0 Å using Cu Kα radiation.

In another embodiment, Form A is characterized as having a PXRD pattern with d-spacings at 7.7, 7.0, and 6.4 Å using Cu Kα radiation.

In another embodiment, Form A is characterized as having a PXRD pattern with at least three d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least four d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least five d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least six d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least seven d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least eight d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least nine d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD pattern with at least ten d-spacings at 13.1, 8.9, 7.7, 7.0, 6.6, 6.43, 6.36, 5.8, 5.6, 5.4, 5.3, 4.9, 4.8, 4.7, 4.6, 4.5, 4.34, 4.27, 4.2, 4.1, 4.0, 3.9, 3.81, 3.76, 3.5, 3.4, 3.2, 3.0, 2.72, 2.66, 2.5, and/or 2.3 Å using Cu Kα radiation.

In another embodiment, Form A is characterized as having a PXRD diffractogram that is essentially the same as the one depicted in FIG. 1.

In another embodiment, Form A is characterized as having an FT-Raman spectrum with peaks at 2989, 2934, 2883, 1685, 1637, 1459, and 930 cm$^{-1}$, wherein the cm$^{-1}$ values are ±4 cm$^{-1}$.

In another embodiment, Form A, characterized as having an FT-Raman spectrum with peaks at 2989, 2960, 2934, 2883, 1685, 1637, 1459, 1417, 1346, 1272, 1199, 1058, 1023, 967, 930, 782, 552, 496, 425, and 342 cm$^{-1}$, wherein the cm$^{-1}$ values are ±4 cm$^{-1}$.

Figure 2:
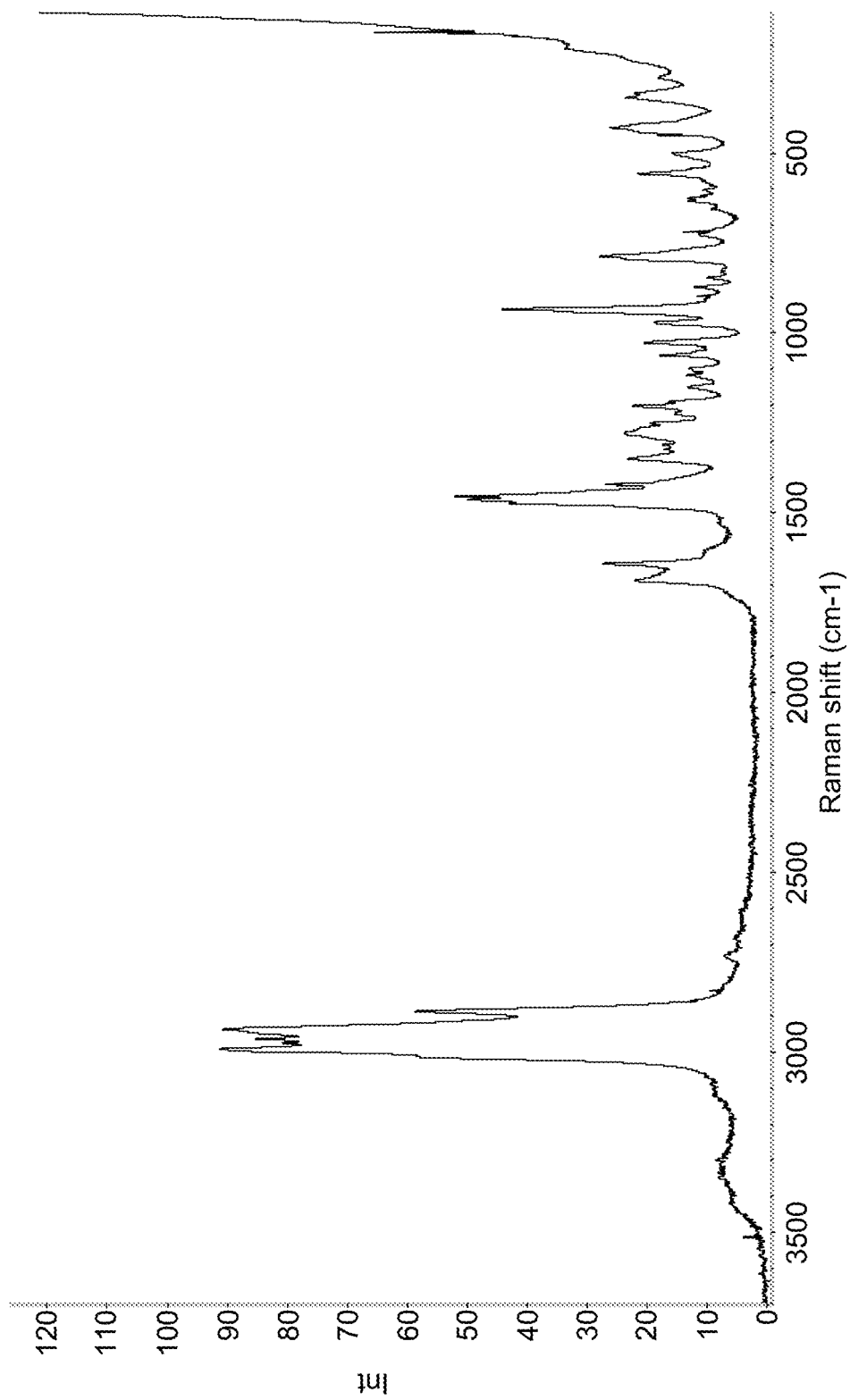
FIG. 2 is a Raman spectrum of Form A.

In another embodiment, Form A is characterized as having a FT-Raman spectrum that is essentially the same as the one depicted in FIG. 2.

In another embodiment, Form A is characterized as having a low frequency (LF) Raman spectrum with peaks at 13, 24, 67, and 77 cm$^{-1}$, wherein the cm$^{-1}$ values are ±4 cm$^{-1}$.

In another embodiment, Form A is characterized as having a LF-Raman spectrum with peaks at 13, 24, 34, 67, 77, 208, 283, 348, 422, 495, and 552 cm$^{-1}$, wherein the cm$^{-1}$ values are ±4 cm$^{-1}$.

Figure 3:
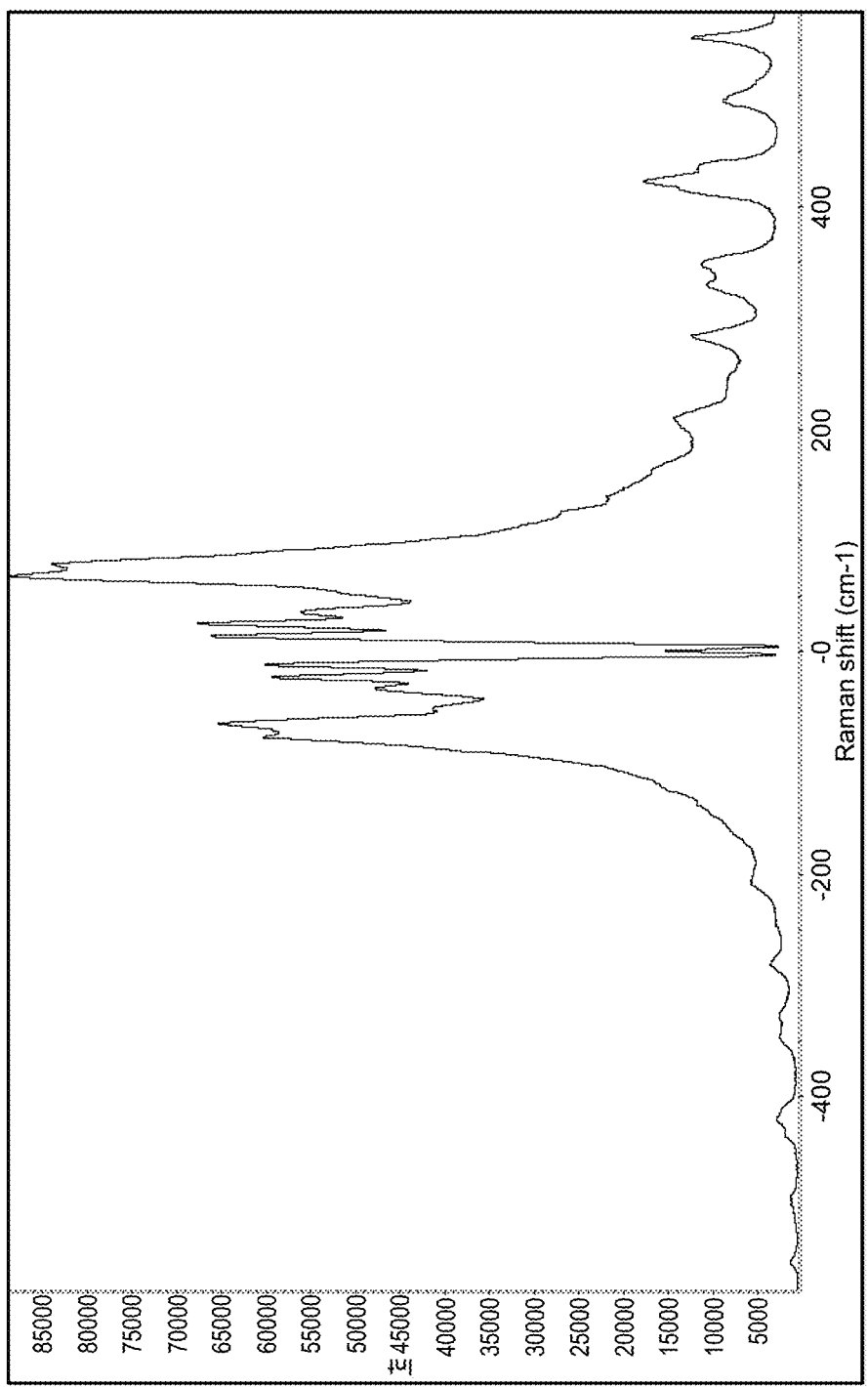
FIG. 3 is a LF-Raman spectrum of Form A.

In another embodiment, Form A is characterized as having a LF-Raman spectrum that is essentially the same as the one depicted in FIG. 3.

In another embodiment, Form A is characterized as having a $^{13}$C solid-state nuclear magnetic resonance (ssNMR) spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 ppm.

In another embodiment, Form A is characterized as having a ssNMR spectrum with 18 peaks, wherein the Δ from the most downfield peak to (i) the second most downfield peak is 1.8 ppm; (ii) the third most downfield peak is 2.2 ppm; (iii) the fourth most downfield peak is 2.5 ppm; (iv) the fifth most downfield peak is 2.7 ppm (v) the sixth most downfield peak is 14.4 ppm; (vi) the seventh most downfield peak is 14.8 ppm; (vii) the eight most downfield peak is 14.9 ppm; (viii) the ninth most downfield peak is 111.9 ppm; (ix) the tenth most downfield peak is 112.3 ppm; (x) the eleventh most downfield peak is 121.1 ppm; (xi) the twelfth most downfield peak is 121.5 ppm; (xii) the thirteenth most downfield peak is 133.1 ppm; (xiii) the fourteenth most downfield peak is 139.4 ppm; (xiv) the fifteenth most downfield peak is 146.3 ppm; (xv) the sixteenth most downfield peak is 154.4 ppm; (xvi) the seventeenth most downfield peak is 156.2 ppm; and/or (xvii) the Δ from the most downfield peak to the most upfield peak is 158.6 ppm, or any combination thereof. See, e.g., Tables 5 and 6.

Figure 4:
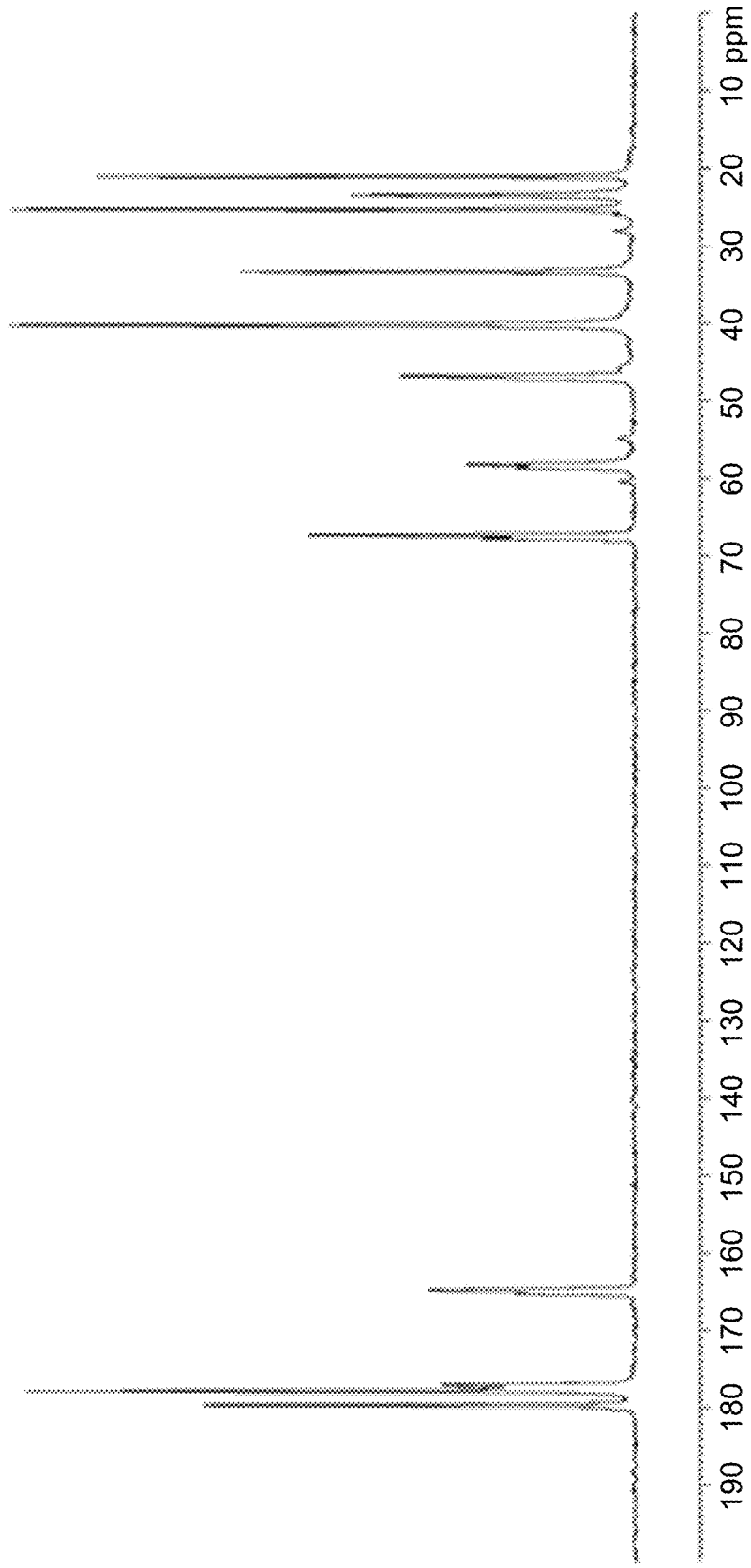
FIG. 4 is ssNMR spectrum of Form A.

In another embodiment, Form A is characterized as having a ssNMR spectrum that is essentially the same as the one depicted in FIG. 4.

In another embodiment, Form A is characterized as having a melting point with an onset temperature of 71.71° C. and a peak temperature of 72.06° C. based on differential scanning calorimetry (DSC).

Figure 5:
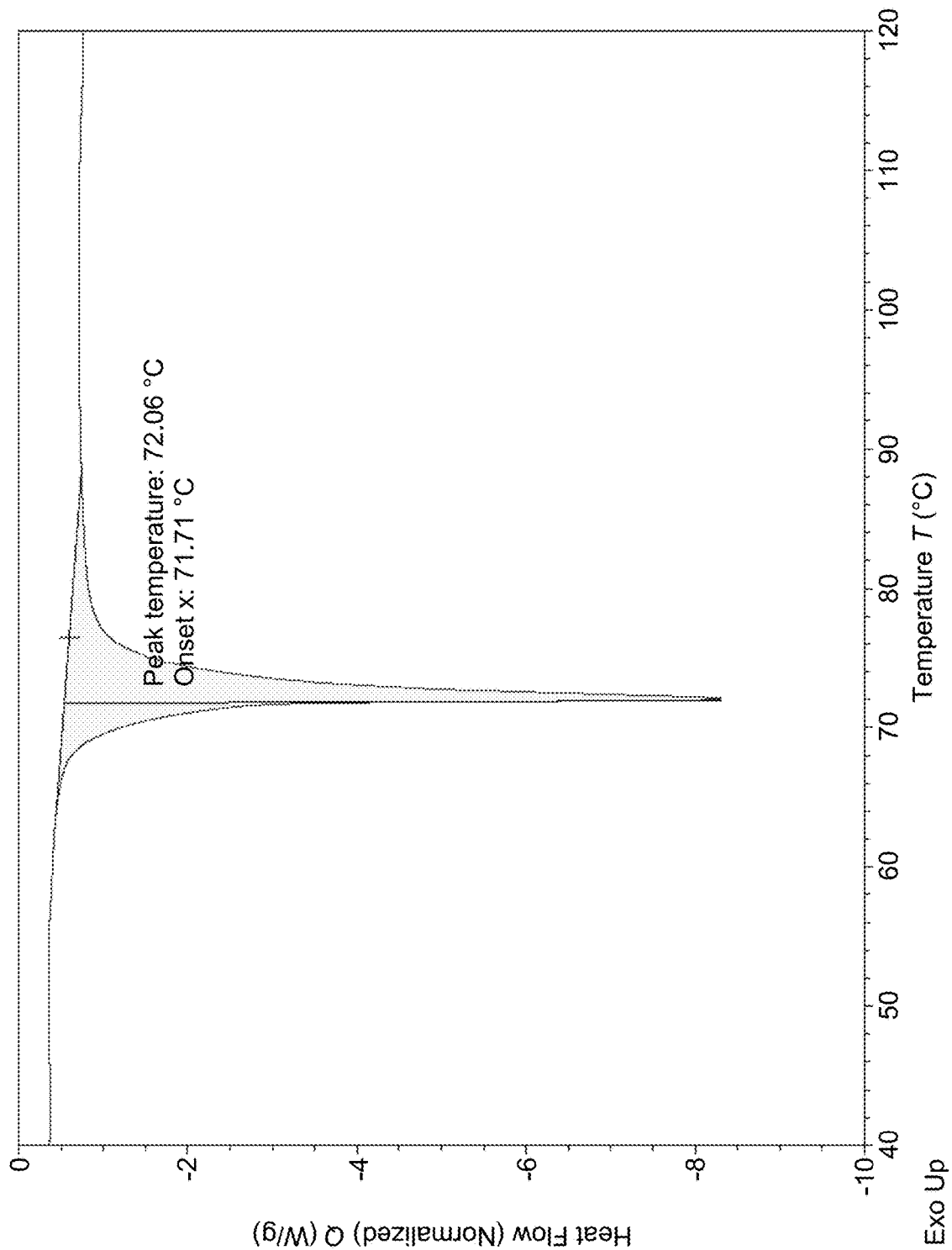
FIG. 5 is a DSC thermogram of Form A.

In another embodiment, Form A is characterized as having a DSC thermogram that is essentially the same as the one depicted in FIG. 5

In another embodiment, Form A is characterized as having an infrared (IR) spectrum with peaks at 1678, 1636, 1589, 1525, 1214, and 1196 cm$^{-1}$, wherein the cm$^{-1}$ values are ±4 cm$^{-1}$.

In another embodiment, Form A is characterized as having an IR spectrum with peaks at 3560, 3400, 3343, 3296, 2881-3012, 1678, 1636, 1589, 1525, 1458, 1435, 1413, 1376, 1352, 1292, 1255, 1214, 1196, 1142, 1120, 1015, 964, 924, 898, 827, 843, 777, 649, 599, 576, 551, 502, and 426 cm$^{-1}$, wherein the cm$^{-1}$ values are ±4 cm$^{-1}$.

Figure 6:
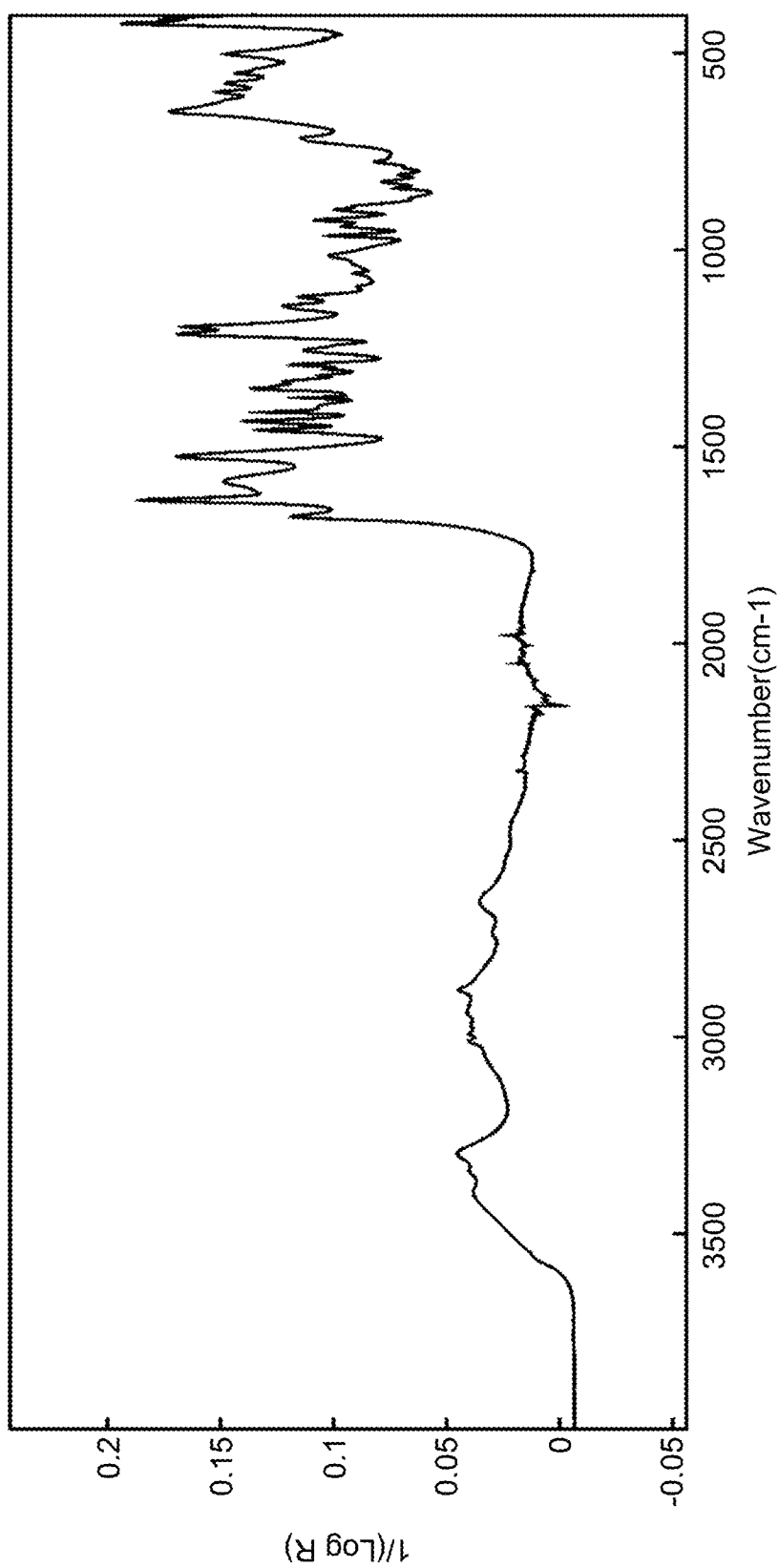
FIG. 6 is an IR spectrum of Form A.

In another embodiment, Form A is characterized as having an IR spectrum that is essentially the same as the one depicted in FIG. 6.

In another embodiment, Form A is characterized as having a near-infrared (NIR) spectrum with peaks at 5145, 4630, and 4423 cm$^{-1}$, wherein the cm$^{-1}$ values are ±4 cm$^{-1}$.

In another embodiment, Form A is characterized as having a NIR spectrum with peaks at 5908, 5796, 5145, 4875, 4630, 4423, and 4298 cm$^{-1}$, wherein the cm$^{-1}$ values are ±4 cm$^{-1}$.

Figure 7:
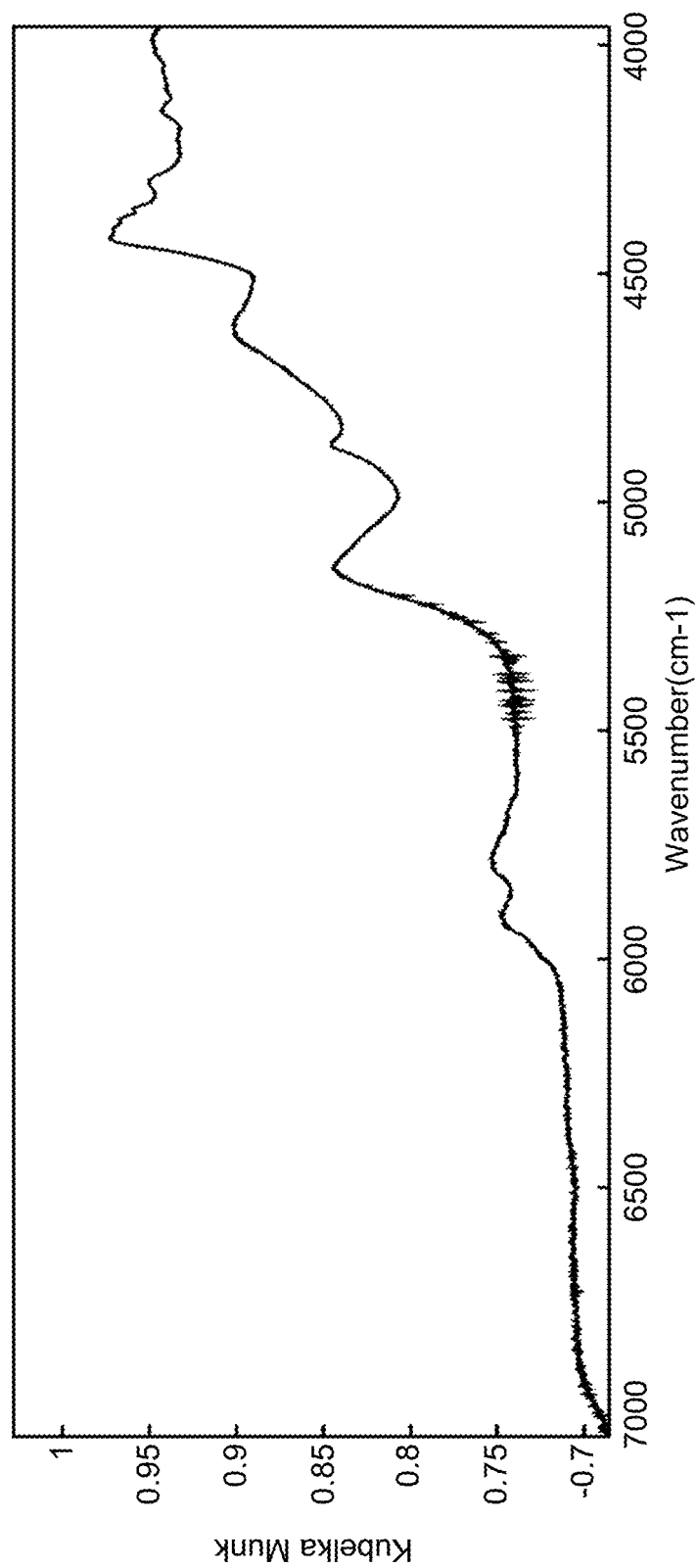
FIG. 7 is NIR spectrum of Form A.

In another embodiment, Form A is characterized as having a NIR spectrum that is essentially the same as the one depicted in FIG. 7.

In another embodiment, the trofinetide polymorph, e.g., Form A, is characterized as comprising about 1% to about 10%, e.g., about 10%, about 9%, about 8%, about 7%, about 6%, about 5%, about 4%, about 3%, about 2%, or about 1%, by weight, of any other physical forms, e.g., crystalline or amorphous forms, of trofinetide or trofinetide hydrate.

In another embodiment, the trofinetide polymorph, e.g., Form A, is characterized as comprising about 0.1% to about 1%, e.g., about 1%, about 0.9%, about 0.8%, about 0.7%, about 0.6%, about 0.5%, about 0.4%, about 0.3%, about 0.2%, or about 0.1%, by weight, of any other physical forms of trofinetide or trofinetide hydrate.

In another embodiment, the trofinetide polymorph is characterized as comprising no PXRD-detectable amount of any other physical forms of trofinetide or trofinetide hydrate. In another embodiment, the trofinetide polymorph is Form A.

In another embodiment, the trofinetide polymorph has an average particle size distribution of about 10 μm to about 500 μm e.g., about 500 μm, about 400 μm, about 300 μm, about 200 μm, about 100 μm, about 90 μm, about 80 μm, about 70 μm, about 60 μm, about 50 μm, about 40 μm, about 30 μm, about 20 μm, or about 10 μm. In another embodiment, the trofinetide polymorph is Form A.

In another embodiment, the trofinetide polymorph has average particle size distribution is about 1 μm to about 10 μm, e.g., about 10 μm, about 9 μm, about 8 μm, about 7 μm, about 6 μm, or about 5 μm, about 4 μm, about 3 μm, about 2 μm, or about 1 μm. In another embodiment, the trofinetide polymorph is Form A.

In another embodiment, the trofinetide polymorph has an average particle size distribution is about 1 μm or less, e.g., about 0.9 μm, about 0.8 μm, about 0.7 μm, about 0.6 μm, about 0.5 μm, about 0.4 μm, about 0.3 μm, about 0.2 μm, about 0.1 μm, about 0.09 μm, about 0.08 μm, about 0.07 μm, about 0.06 μm, about 0.05 μm, about 0.04 μm, about 0.03 μm, about 0.02 μm, or about 0.01 μm or less. In another embodiment, the trofinetide polymorph is Form A.

In another embodiment, the trofinetide polymorph is chemically stable for 3 months of storage at temperature of about 25° C. and a relative humidity of about 60%. In another embodiment, the trofinetide polymorph is Form A.

In another embodiment, the trofinetide polymorph is chemically stable for 6 months of storage at temperature of about 25° C. and a relative humidity of about 60%. In another embodiment, the trofinetide polymorph is Form A.

In another embodiment, the trofinetide polymorph is chemically stable for 12 months or more of storage at temperature of about 25° C. and a relative humidity of about 60%. In another embodiment, the trofinetide polymorph is Form A.

II. Pharmaceutical Compositions and Formulations

In another embodiment, the present disclosure provides a pharmaceutical composition comprising a trofinetide polymorph and one or more pharmaceutically acceptable excipients.

In another embodiment, the present disclosure provides a pharmaceutical formulation comprising a trofinetide polymorph in granular form, wherein the granule optionally comprises one or more pharmaceutically acceptable binders or fillers or a combination thereof. Binders may be used in a total amount of about 1% to about 30% by weight of the granules, e.g., in a total amount of about 5% to about 15% by weight of the granules, e.g., in a total amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of the granules. Fillers may be used in a total about of about 5% to about 80% by weight of the granules, e.g., in a total amount of about 10% to about 60% by weight of the granules, e.g., in a total amount of about 5%, about 10%, about 15%, about 20%, about 25%, about 30%, about 35%, about 40%, about 45%, about 50%, about 55%, about 60%, about 65%, about 70%, about 75%, or about 80% by weight of the granules.

In another embodiment, the binder is acacia, gelatin, hydroxypropyl cellulose, hydroxypropylmethyl cellulose, methyl cellulose, polyethylene glycol (PEG), povidone (polyvinyl pyrrolidone, PVP), sucrose, or starch, or a combination thereof.

In another embodiment, the filler is microcrystalline cellulose.

In another embodiment, the present disclosure provides an aqueous pharmaceutical formulation comprising a trofinetide polymorph dissolved in water and, optionally, one or more additional excipients.

In another embodiment, the water is purified water.

In another embodiment, about 1 gram of the trofinetide polymorph is dissolved in each 5 mL of the water.

In another embodiment, the trofinetide polymorph is Form A.

In another embodiment, pharmaceutical formulation contains from 1% to 99% by weight of the trofinetide polymorph, e.g., about 1%, about 2%, about 3%, about 4%, about 5%, about 6%, about 7%, about 8%, about 9%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. The amount in any particular formulation will depend upon the effective dose of trofinetide, that is, the dose required to elicit the desired level of therapeutic activity. In one embodiment, the pharmaceutical formulation comprises Form A dissolved in water.

III. Methods of Making Pharmaceutical Formulations

In another embodiment, the present disclosure provides methods of making an aqueous pharmaceutical formulation comprising trofinetide, the method comprising dissolving a trofinetide polymorph in water.

In another embodiment, the water is purified water.

In another embodiment, about 1 gram of the trofinetide polymorph is dissolved in each 5 mL of the water.

In another embodiment, the trofinetide polymorph is Form A.

IV. Kits

In another embodiment, the present disclosure provides a kit comprising a trofinetide polymorph packaged in a manner that facilitates its use to practice methods of the present disclosure.

In another embodiment, the kit includes a trofinetide polymorph packaged in a container, such as a sealed bottle or vessel, with a label affixed to the container or and insert included in the kit that describes the use of the trofinetide polymorph to practice a method of the disclosure for treating a disease, disorder, or condition in a subject. In another embodiment, the trofinetide polymorph is packaged in a unit dosage form.

In another embodiment, the kit further comprises instructions for dissolving the trofinetide polymorph in a water to provide an aqueous pharmaceutical formulation.

In another embodiment, the kit further comprises an insert, e.g., instructions for administering the trofinetide polymorph or aqueous pharmaceutical formulation to a subject having a disease, disorder or condition. In another embodiment, the disease, disorder or condition is traumatic brain injury. In another embodiment, the disease, disorder or condition is a neurodevelopmental disorder. In another embodiment, the neurodevelopmental disorder is Rett Syndrome, Fragile X Syndrome, or autism spectrum disorder.

In another embodiment, the trofinetide polymorph is Form A.

V. Methods of Treating a Disease, Disorder, or Condition

In another embodiment, the present disclosure provides a method of treating a disease, disorder or condition in a subject in need thereof, the method comprising administering a aqueous pharmaceutical formulation comprising a trofinetide polymorph dissolved in water to the subject. In another embodiment, the disease, disorder or condition is traumatic brain injury. In another embodiment, the disease, disorder or condition is a neurodevelopmental disorder. In another embodiment, the neurodevelopmental disorder is Rett Syndrome, Fragile X Syndrome, or autism spectrum disorder.

In another embodiment, the aqueous pharmaceutical formulation is a solution for oral administration.

In another embodiment, the water is purified water.

In another embodiment, about 1 gram of the trofinetide polymorph is dissolved in each 5 mL of the water.

In another embodiment, the trofinetide polymorph is Form A.

VI. Methods of Making Crystalline Trofinetide or Trofinetide Hydrate

In another embodiment, the present disclosure provides methods of making a trofinetide polymorph.

In another embodiment, the present disclosure provides a method of making Form A.

In another embodiment, the present disclosure provides a method of making Form A, the method comprising i) adding ethanol to an aqueous solution of trofinetide at about 25° C.; and ii) cooling the solution to about 0° C. In another embodiment, the water:ethanol ratio is approximately 3:7 w/w. In another embodiment, the solution concentration of trofinetide is about 15% w/w.

In another embodiment, the method of making Form A further comprises adding Form A to seed the solution to give a slurry.

In another embodiment, the method of making Form A further comprises isolating, e.g., by filtration, the solid thus obtained to give a wet cake comprising Form A.

In another embodiment, the method of making Form A further comprises washing the wet cake comprising Form A with precooled ethanol at about 0° C.

In another embodiment, the method of making Form A further comprises drying the wet cake comprising Form A under vacuum.

VII. Definitions

The term "trofinetide" as used herein refers to glycyl-L-2-methylprolyl-L-glutamic acid of Formula I:

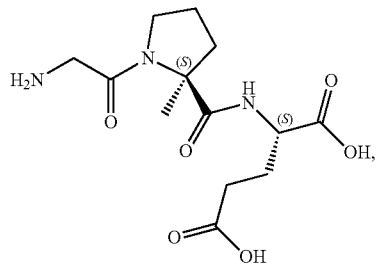

wherein each stereocenter is in the S configuration. The IUPAC name of trofinetide is (2S)-2-[[(2S)-1-(2-aminoacetyl)-2-methylpyrrolidine-2-carbonyl]amino]pentanedioic acid. Trofinetide is also referred to as "G-2-MePE," "H-Gly-MePro-Glu-OH," or "Gly-MePro-Glu-OH."

Trofinetide may form crystalline solids that incorporate solvates, e.g., water or methanol, into the crystal lattice without chemical alteration of the trofinetide molecule. The term "trofinetide hydrate" is represented by the formula: trofinetide.$xH_2O$, wherein x is the ratio of $H_2O$ moles per mole of trofinetide. Trofinetide hydrate does not have to contain water in stoichiometric amounts, e.g., x can be about 2.5. In one embodiment, x is about 1 to about 5. In another embodiment, x is about 2 to about 4. In another embodiment, x is about 2.5 to about 3.5. In another embodiment, x is about 2. In another embodiment x is about 2.5. In another embodiment x is about 3. In another embodiment, x is about 3.5. In another embodiment, x is about 4. In another embodiment, x is about 4.5.

As used herein, the term "substantially pure" with reference to a trofinetide polymorph means that the crystalline material comprises about 10% or less, e.g., about 1% to about 10%, e.g., about 9%, about 8%, about 7%, about 6%, about 5%, about 4%, about 3%, about 2%, or about 1%, by weight of any other crystalline or amorphous form(s) of trofinetide or trofinetide hydrate. In another embodiment, the trofinetide polymorph is substantially pure Form A.

As used herein, the term "pure" with reference to a trofinetide polymorph means that the crystalline material comprises about 1% or less, e.g., about 0.1% to about 1%, e.g., about 1%, about 0.9%, about 0.8%, about 0.7%, about 0.6%, about 0.5%, about 0.4%, about 0.3%, about 0.2%, or about 0.1%, or less, by weight of any other crystalline or amorphous form(s) of trofinetide. In one embodiment, the crystalline trofinetide polymorph e.g., Form A, contains no PXRD-detectable amount of any other crystalline or amorphous form(s) of trofinetide or trofinetide hydrate. In another embodiment, the trofinetide polymorph is pure Form A.

As used herein, the term "amorphous" refers to a solid form of trofinetide or trofinetide hydrate that lacks the long-range order characteristic of a crystal, i.e., the solid is non-crystalline.

As used herein, the term "essentially the same" with reference to PXRD peak positions and/or relative intensities means that peak position and/or intensity variabilities are taken into account when comparing PXRD diffractograms. Likewise, term "essentially the same" with reference to Raman or IR peak positions means that peak position variabilities are taken into account when comparing Raman or IR spectra. For example, PXRD peak positions can show, e.g., inter-apparatus variability, e.g., as much as 0.2° 2Θ, i.e., ±0.2 degrees 2Θ; Raman and IR peak positions can show, e.g., inter-apparatus variability, e.g., as much 4 $cm^{-1}$, i.e., ±4 $cm^{-1}$. Relative peak intensities, for example, in a PXRD diffractogram, can also show inter-apparatus variability due to degree of crystallinity, orientation, prepared sample surface, and other factors known to those skilled in the art, and should be taken as qualitative measures only.

As used herein, the term "micronization" refers to a process or method by which the size of a population of particles is reduced, typically to the micron scale.

As used herein, the term "micron" or "μm" refer to "micrometer," which is $1 \times 10^{-6}$ meter.

As used herein, the term "therapeutically effective amount," refers to the amount of trofinetide sufficient to treat one or more symptoms of a disease, condition, injury, or disorder, or prevent advancement of disease, condition, injury, or disorder, or cause regression of the disease, condition, injury, or disorder.

As used herein, the term "chemically stable" and the like with reference to a trofinetide polymorph means that the trofinetide crystalline solid shows less than 0.5% chemical degradation, e.g., less than 0.4%, less than 0.3%, less than 0.2%, less than 0.1%, or less than 0.05% chemical degradation, after storage at temperature of about 25° C. and a relative humidity of about 60% for at least 3 months In determining the amount of degradation, the appearance of one or more chemical impurities can be measured and/or the disappearance of trofinetide can be measured using methods, e.g., HPLC, known in the art.

The terms "a" and "an" refer to one or more than one.

The term "about" as used herein, includes the recited number±10%. Thus, "about 10" means 9 to 11.

As used herein, the term "average particle size distribution" or "$D_{50}$" is the diameter where 50 mass-% of the particles have a larger equivalent diameter, and the other 50 mass-% have a smaller equivalent diameter as determined by laser diffraction, e.g., in Malvern Master Sizer Microplus equipment or its equivalent.

As used herein, the term "excipient" refers to any ingredient in or added to give a pharmaceutical formulation suitable for administration to a subject, e.g., a solution for oral administration, other than the trofinetide polymorph. An excipient is typically an inert substance, e.g., water, added to a composition to facilitate processing, handling, dissolution, administration, etc. of the trofinetide polymorph. Useful excipients include, but are not limited to, adjuvants, antiadherents, binders, carriers, disintegrants, fillers, flavors, colors, diluents, lubricants, glidants, preservatives, sorbents, solvents, surfactants, and sweeteners.

Conventional pharmaceutical excipients are well known to those skilled in the art. A wide variety of pharmaceutical excipients can be used in admixture with a trofinetide polymorph, including water, and others listed in the *Handbook of Pharmaceutical Excipients*, Pharmaceutical Press 4th Ed. (2003), and *Remington: The Science and Practice of Pharmacy*, Lippincott Williams & Wilkins, 21st ed. (2005). In one embodiment, the composition comprises Form A dissolved in water.

As used herein, the term "subject" refers to an animal, e.g., human or veterinary animal, e.g., cow, sheep, pig, horse, dog, or cat. In one embodiment, the subject is a human.

As used herein, the term "container" means any receptacle and closure therefore suitable for storing, shipping, dispensing, and/or handling a pharmaceutical product or excipient.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

As used herein, the term "and/or" is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

VII. Particular Embodiments

The disclosure provides the following particular embodiments.

Embodiment 1. Crystalline trofinetide.xH$_2$O, wherein x is about 2 to about 4, characterized as having:

(i) a powder x-ray diffraction pattern with peaks at 6.8, 11.5, 12.6, 13.8, and 16.8 degrees 2Θ using Cu Kα radiation, wherein the 2Θ values are ±0.2 degrees 2Θ; or (ii) a powder x-ray diffraction pattern with d-spacings at 13.1, 7.7, 7.0, 6.4, and 5.3 Å using Cu Kα radiation; or (iii) a FT-Raman spectrum with peaks at 2989, 2934, 2883, 1685, 1637, 1459, and 930 cm$^{-1}$, wherein the cm$^{-1}$ values are ±4 cm$^{-1}$; or (iv) a low frequency (LF) Raman spectrum with peaks at 13, 24, 67, and 77 cm$^{-1}$, wherein the cm$^{-1}$ values are ±4 cm$^{-1}$; or (v) a $^{13}$C solid-state nuclear magnetic resonance spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 μm; or (vi) a $^{13}$C solid-state nuclear magnetic resonance spectrum with 18 peaks, wherein the Δ from the furthest downfield peak to: (i) the second furthest downfield peak is 1.8 ppm; (ii) the third furthest downfield peak is 2.2 ppm; (iii) the fourth furthest downfield peak is 2.5 ppm; (iv) the fifth furthest downfield peak is 2.7 ppm (v) the sixth furthest downfield peak is 14.4 ppm; (vi) the seventh furthest downfield peak is 14.8 ppm; (vii) the eight furthest downfield peak is 14.9 ppm; (viii) the ninth furthest downfield peak is 111.9 ppm; (ix) the tenth furthest downfield peak is 112.3 ppm; (x) the eleventh furthest downfield peak is 121.1 ppm; (xi) the twelfth furthest downfield peak is 121.5 ppm; (xii) the thirteenth furthest downfield peak is 133.1 ppm; (xiii) the fourteenth furthest downfield peak is 139.4 ppm; (xiv) the fifteenth furthest downfield peak is 146.3 ppm; (xv) the sixteenth furthest downfield peak is 154.6 ppm; (xvi) the seventeenth furthest downfield peak is 156.2 ppm; and/or (xvii) the Δ from the furthest downfield peak to the furthest upfield peak is 158.6 ppm, or any combination thereof; or (vii) a melting point with an onset temperature of 71.71° C. and a peak temperature of 72.06° C. based on differential scanning calorimetry; or (viii) an infrared (IR) spectrum with peaks at 1678, 1636, 1589, 1525, 1214, and 1196 cm$^{-1}$, wherein the cm$^{-1}$ values are ±4 cm$^{-1}$; or (ix) a near-infrared (NIR) spectrum with peaks at 5145, 4630, and 4423 cm$^{-1}$, wherein the cm$^{-1}$ values are ±4 cm$^{-1}$; or a combination thereof.

Embodiment 2. Crystalline trofinetide.xH$_2$O, wherein x is about 2 to about 4, characterized as having:

(i) a powder x-ray diffraction pattern with peaks at 6.8, 11.5, 12.6, 13.8, and 16.8 degrees 2Θ using Cu Kα radiation, wherein the 2Θ values are ±0.2 degrees 2Θ; and/or (ii) a powder x-ray diffraction pattern with d-spacings at 13.1, 7.7, 7.0, 6.4, and 5.3 Å using Cu Kα radiation; and/or (iii) a FT-Raman spectrum with peaks at 2989, 2934, 2883, 1685, 1637, 1459, and 930 cm$^{-1}$, wherein the cm$^{-1}$ values are ±4 cm$^{-1}$; and/or (iv) a low frequency (LF) Raman spectrum with peaks at 13, 24, 67, and 77 cm$^{-1}$, wherein the cm$^{-1}$ values are ±4 cm$^{-1}$; and/or (v) a $^{13}$C solid-state nuclear magnetic resonance spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 μm; and/or (vi) a $^{13}$C solid-state nuclear magnetic resonance spectrum with 18 peaks, wherein the Δ from the furthest downfield peak to: (i) the second furthest downfield peak is 1.8 ppm; (ii) the third furthest downfield peak is 2.2 ppm; (iii) the fourth furthest downfield peak is 2.5 ppm; (iv) the fifth furthest downfield peak is 2.7 ppm (v) the sixth furthest downfield peak is 14.4 ppm; (vi) the seventh furthest downfield peak is 14.8 ppm; (vii) the eight furthest downfield peak is 14.9 ppm; (viii) the ninth furthest downfield peak is 111.9 ppm; (ix) the tenth furthest downfield peak is 112.3 ppm; (x) the eleventh furthest downfield peak is 121.1 ppm; (xi) the twelfth furthest downfield peak is 121.5 ppm; (xii) the thirteenth furthest downfield peak is 133.1 ppm; (xiii) the fourteenth furthest downfield peak is 139.4 ppm; (xiv) the fifteenth furthest downfield peak is 146.3 ppm; (xv) the sixteenth furthest downfield peak is 154.6 ppm; (xvi) the seventeenth furthest downfield peak is 156.2 ppm; and/or (xvii) the Δ from the furthest downfield peak to the furthest upfield peak is 158.6 ppm, or any combination thereof; and/or (vii) a melting point with an onset temperature of 71.71° C. and a peak temperature of 72.06° C. based on differential scanning calorimetry; and/or (viii) an infrared (IR) spectrum with peaks at 1678, 1636, 1589, 1525, 1214, and 1196 cm$^{-1}$, wherein the cm$^{-1}$ values are ±4 cm$^{-1}$; and/or (ix) a near-infrared (NIR) spectrum with peaks at 5145, 4630, and 4423 cm$^{-1}$, wherein the cm$^{-1}$ values are ±4 cm$^{-1}$; and/or a combination thereof.

Embodiment 3. The crystalline trofinetide.xH$_2$O of Embodiments 1 or 2, characterized as having a powder x-ray diffraction pattern with peaks at 6.8, 11.5, 12.6, 13.8, and 16.8 degrees 2Θ using Cu Kα radiation, wherein the 2Θ values are ±0.2 degrees 2Θ.

Embodiment 4. The crystalline trofinetide.xH$_2$O of any one of Embodiments 1-3, characterized as having a powder x-ray diffraction pattern with d-spacings at 13.1, 7.7, 7.0, 6.4, and 5.3 Å using Cu Kα radiation.

Embodiment 5. The crystalline trofinetide.xH$_2$O of any one of Embodiments 1-4, characterized as having an FT-Raman spectrum with peaks at 2989, 2934, 2883, 1685, 1637, 1459, and 930 cm$^{-1}$, wherein the cm$^{-1}$ values are ±4 cm$^{-1}$.

Embodiment 6. The crystalline trofinetide.xH$_2$O of any one of Embodiments 1-5, characterized as having a low frequency (LF) Raman spectrum with peaks at 13, 24, 67, and 77 cm$^{-1}$, wherein the cm$^{-1}$ values are ±4 cm-1.

Embodiment 7. The crystalline trofinetide.xH$_2$O of any one of Embodiments 1-6, characterized as having a $^{13}$C solid-state nuclear magnetic resonance spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 μm.

Embodiment 8. The crystalline trofinetide.xH$_2$O of any one of Embodiments 1-7, characterized as having a $^{13}$C solid-state nuclear magnetic resonance spectrum with 18 peaks, wherein the Δ from the furthest downfield peak to: (i) the second furthest downfield peak is 1.8 ppm; (ii) the third furthest downfield peak is 2.2 ppm; (iii) the fourth furthest downfield peak is 2.5 ppm; (iv) the fifth furthest downfield peak is 2.7 ppm (v) the sixth furthest downfield peak is 14.4 ppm; (vi) the seventh furthest downfield peak is 14.8 ppm; (vii) the eight furthest downfield peak is 14.9 ppm; (viii) the ninth furthest downfield peak is 111.9 ppm; (ix) the tenth furthest downfield peak is 112.3 ppm; (x) the eleventh furthest downfield peak is 121.1 ppm; (xi) the twelfth furthest downfield peak is 121.5 ppm; (xii) the thirteenth furthest downfield peak is 133.1 ppm; (xiii) the fourteenth furthest downfield peak is 139.4 ppm; (xiv) the fifteenth furthest downfield peak is 146.3 ppm; (xv) the sixteenth furthest downfield peak is 154.6 ppm; (xvi) the seventeenth furthest downfield peak is 156.2 ppm; and/or (xvii) the Δ from the furthest downfield peak to the furthest upfield peak is 158.6 ppm, or any combination thereof.

Embodiment 9. The crystalline trofinetide.xH$_2$O of any one of Embodiments 1-8, characterized as having a melting point with an onset temperature of 71.71° C. and a peak temperature of 72.06° C. based on differential scanning calorimetry.

Embodiment 10. The crystalline trofinetide.xH$_2$O of any one of Embodiments 1-8, characterized as having an infrared (IR) spectrum with peaks at 1678, 1636, 1589, 1525, 1214, and 1196 cm$^{-1}$, wherein the cm$^{-1}$ values are ±4 cm$^{-1}$.

Embodiment 11. The crystalline trofinetide.xH$_2$O of any one of Embodiments 1-10, characterized as having a near-infrared (NIR) spectrum with peaks at 5145, 4630, and 4423 cm$^{-1}$, wherein the cm$^{-1}$ values are ±4 cm$^{-1}$.

Embodiment 12. The crystalline trofinetide.xH$_2$O of any one of Embodiments 1-11 having average particle size distribution of about 10 μm to about 500 μm.

Embodiment 13. The crystalline trofinetide.xH$_2$O of any one of Embodiments 1-12, wherein x is about 2.5 to about 3.5.

Embodiment 14. The crystalline trofinetide.xH$_2$O of any one of Embodiments 1-12, wherein x is about 2.

Embodiment 15. The crystalline trofinetide.xH$_2$O of any one of Embodiments 1-12, wherein x is about 2.5.

Embodiment 16. The crystalline trofinetide.xH$_2$O of any one of Embodiments 1-12, wherein x is about 3.

Embodiment 17. The crystalline trofinetide.xH$_2$O of any one of Embodiments 1-12, wherein x is about 3.5.

Embodiment 18. The crystalline trofinetide.xH$_2$O of any one of Embodiments 1-12, wherein x is about 4.

Embodiment 19. A pharmaceutical composition comprising the crystalline trofinetide.xH$_2$O of any one of Embodiments 1-18 and a pharmaceutically acceptable excipient.

Embodiment 20. The pharmaceutical composition of Embodiment 19 in granular form.

Embodiment 21. An aqueous pharmaceutical formulation comprising the crystalline trofinetide.xH$_2$O of any one of Embodiments 1-18 dissolved in water.

Embodiment 22. The aqueous pharmaceutical formulation of Embodiment 15, wherein about 1 gram of crystalline trofinetide.xH$_2$O is dissolved in each 5 mL of the water.

Embodiment 23. A method of making the aqueous pharmaceutical formulation of Embodiments 21 or 22, the method comprising admixing the crystalline trofinetide.xH$_2$O and water.

Embodiment 24. A kit comprising the crystalline trofinetide.xH$_2$O of any one of Embodiments 1-18 and instructions for dissolving the crystalline trofinetide.xH$_2$O in a water to provide an aqueous pharmaceutical formulation.

Embodiment 25. The kit of Embodiment 24 further comprising instructions for administering the aqueous pharmaceutical formulation to a subject having a disease, disorder or condition.

Embodiment 26. The kit of Embodiment 25, wherein the disease, disorder or condition is traumatic brain injury.

Embodiment 27. The kit of Embodiment 25, wherein the disease, disorder or condition is a neurodevelopmental disorder.

Embodiment 28. The kit of Embodiment 27, wherein the neurodevelopmental disorder is Rett Syndrome, Fragile X Syndrome, or autism spectrum disorder.

Embodiment 29. A method of treating a disease, disorder or condition in a subject in need thereof, the method comprising administering the pharmaceutical composition of Embodiments 19 or 20, or the aqueous pharmaceutical formulation of Embodiments 21 or 22 to the subject.

Embodiment 30. The method of Embodiment 29, wherein the disease, disorder or condition is traumatic brain injury.

Embodiment 31. The method of Embodiment 29, wherein the disease, disorder or condition is a neurodevelopmental disorder.

Embodiment 32. The method of Embodiment 31, wherein the neurodevelopmental disorder is Rett Syndrome, Fragile X Syndrome, or autism spectrum disorder.

Embodiment 33. The method of Embodiment 29, wherein the disease, disorder or condition is Rett Syndrome.

Embodiment 34. The pharmaceutical composition of Embodiments 19 or 20, or the aqueous pharmaceutical formulation of Embodiments 21 or 22 for use in treating a disease, disorder or condition in a subject in need thereof.

Embodiment 35. The composition or formulation of Embodiment 34, wherein the disease, disorder or condition is traumatic brain injury.

Embodiment 36. The composition or formulation of Embodiment 34, wherein the disease, disorder or condition is a neurodevelopmental disorder.

Embodiment 37. The composition or formulation of Embodiment 36, wherein the neurodevelopmental disorder is Rett Syndrome, Fragile X Syndrome, or autism spectrum disorder.

Embodiment 38. The composition or formulation of Embodiment 34, wherein the disease, disorder or condition is Rett Syndrome.

Embodiment 39. Use of the Trofinetide of any one of Embodiments 1-18, or the pharmaceutical composition of Embodiments 19 or 20, or the aqueous pharmaceutical formulation of Embodiments 21 or 22 in the manufacture of a medicament for a disease, disorder or condition in a subject in need thereof.

Embodiment 40. The use of Embodiment 39, wherein the disease, disorder or condition is traumatic brain injury.

Embodiment 41. The use of Embodiment 39, wherein the disease, disorder or condition is a neurodevelopmental disorder.

Embodiment 42. The use of Embodiment 41, wherein the neurodevelopmental disorder is Rett Syndrome, Fragile X Syndrome, or autism spectrum disorder.

Embodiment 43. The use of Embodiment 39, wherein the disease, disorder or condition is Rett Syndrome.

Embodiment 44. A method of making the crystalline trofinetide.xH$_2$O of any one of Embodiments 1-18, the method comprising i) adding ethanol to an aqueous solution of trofinetide at about 25° C.; ii) cooling the solution to about 0° C.; and iii) isolating the solid thus obtained to crystalline trofinetide.xH$_2$O.

Embodiment 45. The method of Embodiment 44, wherein the water:ethanol ratio is about 3:7 w/w.

EXAMPLES

Instrumentation

Powder X-Ray Diffraction (PXRD or XRPD)

PXRD and XRPD are synonymous terms. The Rigaku Smart-Lab X-ray diffraction system was configured for reflection Bragg-Brentano geometry using a line source X-ray beam. The x-ray source is a Cu Long Fine Focus tube (λ=1.54 Å) that was operated at 40 kV and 44 mA. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1°2Θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40°2Θ using a continuous scan of 6°2Θ per minute with an effective step size of 0.02°2Θ.

Differential Scanning Calorimetry (DSC)

DSC analysis was carried out using a TA Instruments Q2500 Discovery Series instrument. The instrument temperature calibration was performed using indium. The DSC cell was kept under a nitrogen purge of ~50 mL per minute during the analysis. The sample was placed in a standard, crimped, aluminum pan and was heated from approximately 25° C. to 350° C. at a rate of 10° C. per minute.

Dynamic Vapor Sorption (DVS) Analysis

DVS analysis was carried out TA Instruments Q5000 Dynamic Vapor Sorption analyzer. The instrument was calibrated with standard weights and a sodium bromide standard for humidity. Samples were analyzed at 25° C. with a maximum equilibration time of 60 minutes in 10% relative humidity (RH) steps from 5 to 95% RH (adsorption cycle) and from 95 to 5% RH (desorption cycle).

Infrared (IR) Spectroscopy

Infrared spectrum was obtained on a Nicolet 6700 FT-IR system, using a Nicolet SMART iTR attenuated total reflectance device.

Near Infrared (NIR) Spectroscopy

Near Infrared spectrum was obtained on a Nicolet iS50 IR system. About 1% w/w of trofinetide Form A in dried KBr was placed in DRIFT (diffuse reflectance infrared Fourier transform spectroscopy) macro cup and analyzed in spectral range of 8000 and 400 wavenumbers.

FT-Raman Spectroscopy

Fourier transform (FT) Raman spectrum was acquired on a Nicolet model 6700 spectrometer interfaced to a Nexus Raman accessory module. This instrument is configured with a Nd:YAG laser operating at 1024 nm, a CaF$_2$ beamsplitter, and a indium gallium arsenide detector. OMNIC 8.1 software was used for control of data acquisition and processing of the spectra. Samples were packed into a 3-inch glass NMR tube for analysis.

Low Frequency (LF) Raman Spectroscopy

Low frequency Raman spectra were obtained using a Renishaw inVia Raman microscope equipped with an Ondax THz-Raman system (TR-PROBE; excitation laser 853.1 nm, notch filter). The sample powder was analyzed in the open air using the probe tip attachment. Spectra were acquired using a static scan centered at 36 cm$^{-1}$ to collect over the spectral range −575 to 575 cm$^{-1}$ with 100% power, an exposure time of one second, and 32 accumulations. The wavelength calibration was confirmed using a sulfur reference standard. Data acquisition was performed using WiRE 3.4 software.

Karl Fischer (KF) Analyses

Karl Fischer analyses were carried out using a Mettler-Toledo C20 Coulometric KF titrator. The instrument was calibrated using a Hydranal water standard containing 1% water. The titrant was a Hydranal methanol solution.

$^{13}$C Solid-State Nuclear Magnetic Resonance (NMR) Spectroscopy

The solid-state $^{13}$C cross polarization magic angle spinning (CPMAS) experiments were carried out on a Bruker Avance II 400 spectrometer equipped with Doty probe (DSI-1630) 1H(19F)/X double resonance. The sample (109 mg) was packed into a 4-mm 4 mm silicon nitride rotor closed with Kel-F end caps for subsequent data acquisition. Adamantane, set to methylene signal of adamantane at 38.48 ppm on the TMS scale, was used as an external standard. Acquisition and processing parameters used are shown in the table below.

| Nucleus | $^{13}$C |
|---|---|
| Temperature (K) | 297 |
| Observe Frequency (MHz) | 100.6 |
| Dwell Time (μsec) | 19.8 |
| Acquisition Time (msec) | 81 |
| Recycle Delay (sec) | 8 |
| Spin Speed (kHz) | 12 |
| Number of Scans | 2048 |

-continued

| Processing Parameters | |
|---|---|
| Reference | external |
| Line Broadening (Hz) | 1 |

It is possible to perform the $^{13}$C CPMAS analysis on NMR spectrometers with different magnetic fields, such as 9.4 Tesla (100 MHz for $^{13}$C, 400 MHz for $^{1}$H) or higher. Parameters such as acquisition time, dwell time, recycle delay, spin speed, and number of scans can be modified and optimized depending on the NMR spectrometer Single Crystal Structure Determination X-ray diffraction analysis was performed using Cu Kα radiation ($\lambda$=1.54 Å) at a temperature of 150 K. The monoclinic cell parameters and calculated volume for formula $C_{13}H_{21}N_3O_6 \cdot 3(H_2O)$ are a=18.8946 (8) Å, b=7.2849 (3) Å, c=27.8601 (12) Å, $\beta$=109.8540 (16) °, and V=3606.9 (3) Å$^3$. For Z=8 and a formula weight of 369.37 the calculated density is 1.360 g/cm$^3$.

Example 1

Synthesis and Characterization of Form A

Form A was prepared according to the following methods.

Method 1

Charged 19.9 mg of amorphous trofinetide into a mechanical grinding container with one metal ball. Added 7.6 mg of L-asparagine and 10 microliters of water to the grinding container. The container was sealed and milled for about 20 minutes on Retsch Mill at 100% power level. The resulting solid was removed and placed in a vacuum desiccator to dry overnight. The resulting material was a mixture of Form A and crystalline L-aspartic acid by XRPD.

Method 2

Charged 18.6 mg of amorphous trofinetide into a mechanical grinding container with one metal ball. Added 8.0 mg of L-aspartic acid and 10 microliters of water were added to the grinding container. The container was sealed and milled for about 20 minutes on Retsch Mill. The resulting solid was allowed to dry in an open container before transferring the solids. The resulting material was a mixture of Form A and crystalline L-aspartic acid by XRPD. The same experiment was repeated using 20 mg of trofinetide amorphous form and 1 mg of L-aspartic acid. The resulting material was mostly Form A with a trace amount of crystalline L-aspartic acid by XRPD. This material was used as a seed (3 mg) for another repeat experiment using only amorphous trofinetide (19.7 mg). The resulting solid was Form A by XRPD.

Method 3

A solution of trofinetide (300 mL, 32% w/w of trofinetide amorphous form in water) was charged to absolute ethanol (1200 mL) at ambient temperature. The resulting solution was cooled to 2° C. with stirring (300 rpm). The solution was re-heated to 25° C. (12° C./hr, held for 3 hours), and cooled to 2° C. (6° C./hr). The solid precipitate was filtered, washed with cold ethanol (2° C.) and dried under nitrogen at 70% RH/ambient temperature for 16 hours to remove residual ethanol. The resulting solid was Form A by XRPD.

Method 4

The following steps were used to prepare Form A according to Method 4.

Dissolve 205.7 Kg amorphous trofinetide (KF 5.0%, 195.4 Kg dry basis) in 617 Kg water in a reactor at room temperature.

Add 2808 Kg of ethanol to the solution in the reactor at room temperature with vigorous mixing.

Cool the solution to 0-2° C.

Add 1.0 Kg trofinetide seed to the reactor and age the batch for NLT 6 hours with slow agitation. Crystallization will occur.

Filter the slurry in the reactor, isolating in a filter dryer.

Wash the wet cake with 325 Kg of ethanol precooled to 0-2° C. twice.

Vacuum dry the wet cake until the bulk of the residual solvent has been evaporated, then raise the jacket temperature of the filter dryer to room temperature to complete the drying. 170.0 Kg crystalline trofinetide.xH$_2$O (KF 13.5%, 147.0 Kg dry basis) is isolated (75% yield).

Method 5

The following steps were used to prepare Form A according to Method 5.

Add ethanol (4479 Kg) to an aqueous solution of trofinetide (total weight 1272 Kg, 23.2 w/w % trofinetide, 294.5 Kg trofinetide, 977.5 Kg water) at room temperature with vigorous mixing.

Cool the solution to 0-2° C.

Add 2.5 Kg crystalline trofinetide.xH$_2$O seed to the reactor and age the batch for NLT 6 hours with slow agitation. Crystallization will occur.

Filter the slurry in the reactor, isolating in a filter dryer.

Wash the wet cake with 502 Kg of ethanol precooled to 0-2° C. two times.

Vacuum dry the wet cake until the bulk of the residual solvent has been evaporated, then raise the jacket temperature of the filter dryer to room temperature to complete the drying. 292.0 Kg crystalline trofinetide.xH$_2$O (KF 14.3%, 250.2.0 Kg dry basis) is isolated (85% yield).

Method 6

The following steps were used to prepare Form A according to Method 6.

Dissolve 58.1 g crystalline trofinetide.xH$_2$O (KF 14.0%, 50.0 g dry basis) in 100 g water in reactor 1 at room temperature.

Add 233 g (296 mL) of ethanol to the solution in reactor 1 at room temperature with vigorous mixing. (The water/ethanol ratio is approximately 3/7 w/w, and the target solution concentration is approximately 15% w/w trofinetide).

Transfer 128 g of the solution in reactor 1 to reactor 2 (approximately ⅓ of the solution).

Cool reactor 2 to 0-2° C.

Slurry 0.5 g of trofinetide seed material in 5 g of ethanol/water (95/5 w/w)

Add the trofinetide seed slurry to reactor 2 and age the batch for NLT 2 hours with slow agitation. Nucleation will occur to generate a seed bed.

Transfer the remaining solution from reactor 1 to reactor 2 over NLT two hours, maintaining reactor 2 at 0-2° C. with good mixing.

Charge 334 g (423 mL) ethanol into reactor 1 and cool to 0-2° C.

Transfer the ethanol from reactor 1 to reactor 2 over NLT 2 hours, maintaining reactor 2 at 0-2° C. with good mixing (final water/ethanol ratio is approximately 15/85 w/w).

Age the slurry in reactor 2 for not less than 2 hours at 0-2° C. with good mixing.

Prepare the cake wash solution by mixing 25 g water and 475 g EtOH and cooling to 0-2° C.

Filter the slurry in reactor 2, then wash the wet cake on the filter at 0-2° C.

Vacuum dry the wet cake at 0-2° C. until the bulk of the residual solvent has been evaporated, then raise the batch to room temperature to complete the drying. 53.2 g crystalline trofinetide.xH$_2$O (KF 13.5%, 46.0 g dry basis) is isolated (92% yield).

Figure 8:
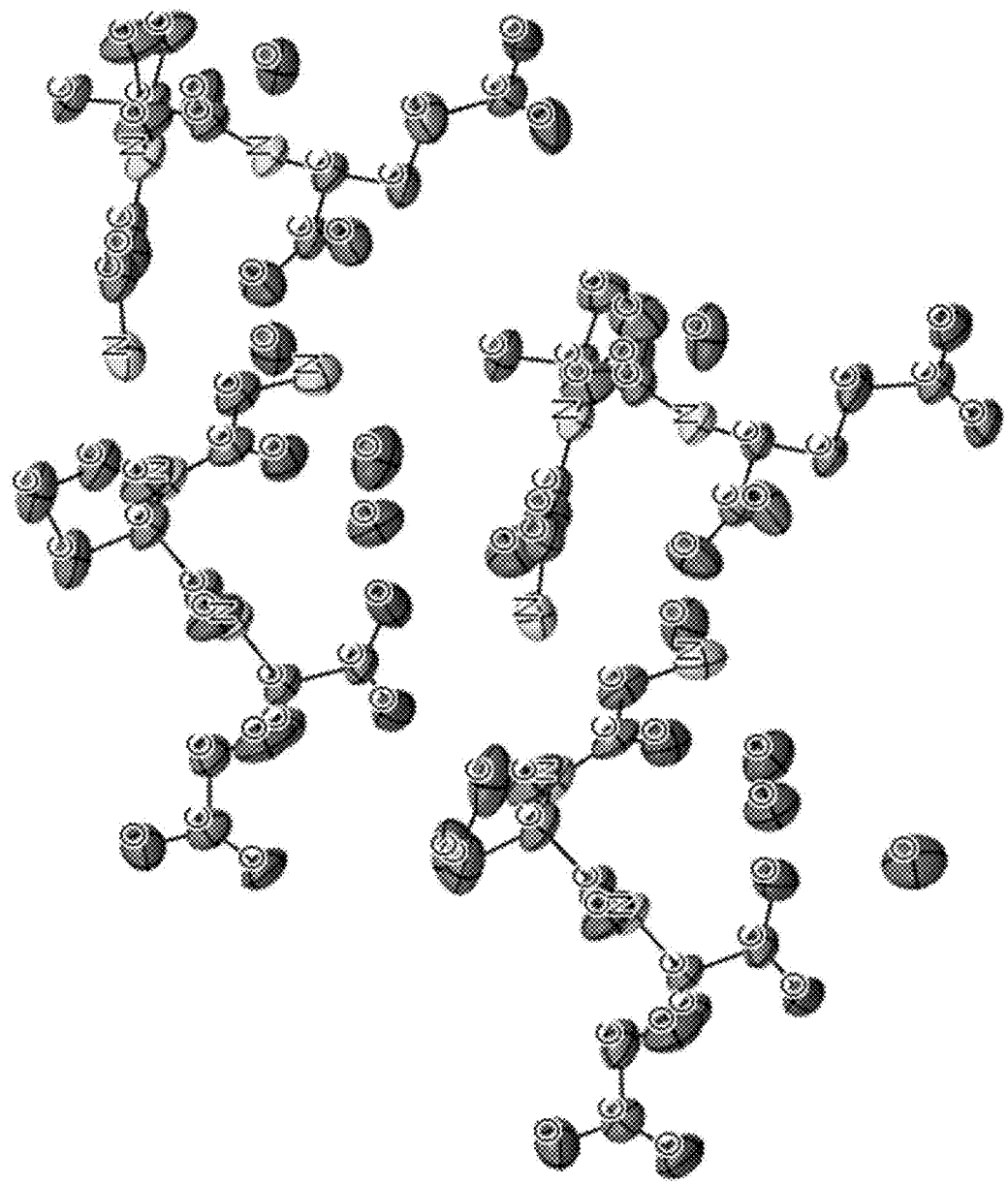
FIG. 8 is a single crystal X-ray diffraction asymmetric unit of Form A. Hydrogen atoms are omitted for clarity.

The structure of Form A was solved by single crystal X-ray diffraction. The structure showed three molecules of water per molecule of trofinetide. The asymmetric unit of Form A is shown in FIG. 8. The hydrogen atoms are omitted for clarity. The structure of Form A shows each of the three water molecules is hydrogen bonded to oxygen or nitrogen atoms of trofinetide. Each of the three water molecules are also hydrogen bonded to the adjacent molecule of water.

The X-ray powder diffraction (XRPD) diffractogram of Form A is shown in FIG. 1. The XRPD peak list (±0.2 degrees 2Θ) is provided in Table 1.

TABLE 1

| degrees 2Θ | d-spacing (angstrom) | Relative Intensity |
|---|---|---|
| 6.8 | 13.1 | 9 |
| 9.9 | 8.9 | 5 |
| 11.5 | 7.7 | 46 |
| 12.6 | 7.0 | 31 |
| 13.5 | 6.6 | 39 |
| 13.8 | 6.43 | 100 |
| 13.9 | 6.36 | 29 |
| 15.4 | 5.8 | 12 |
| 15.8 | 5.6 | 32 |
| 16.3 | 5.4 | 4 |
| 16.8 | 5.3 | 76 |
| 18.2 | 4.9 | 6 |
| 18.7 | 4.8 | 32 |
| 19.0 | 4.7 | 15 |
| 19.2 | 4.6 | 24 |
| 19.8 | 4.5 | 13 |
| 20.4 | 4.34 | 12 |
| 20.8 | 4.27 | 7 |
| 21.2 | 4.2 | 31 |
| 21.5 | 4.1 | 7 |
| 22.3 | 4.0 | 54 |
| 22.8 | 3.9 | 11 |
| 23.3 | 3.81 | 15 |
| 23.6 | 3.76 | 31 |
| 25.4 | 3.5 | 47 |
| 26.4 | 3.4 | 23 |
| 28.1 | 3.2 | 44 |
| 30.2 | 3.0 | 48 |
| 32.9 | 2.72 | 27 |
| 33.7 | 2.66 | 19 |
| 35.4 | 2.5 | 10 |
| 39.1 | 2.3 | 16 |

The Raman spectrum of Form A is shown in FIG. 2. The Raman peak list (±4 cm$^{-1}$) is provided in Table 2.

TABLE 2

| Raman shift (cm$^{-1}$) | Relative Intensity |
|---|---|
| 2989 | strong |
| 2960 | strong |
| 2934 | strong |
| 2883 | strong |
| 1685 | medium |
| 1637 | medium |
| 1459 | strong |
| 1417 | medium |
| 1346 | medium |
| 1272 | medium |
| 1199 | medium |
| 1058 | medium |
| 1023 | medium |
| 967 | medium |
| 930 | strong |
| 782 | medium |
| 552 | medium |
| 496 | medium |
| 425 | medium |
| 342 | medium |

The low frequency (LF) Raman spectrum of Form A is shown in FIG. 3. The LF Raman peak list (±4 cm$^{-1}$) is provided in Table 3.

TABLE 3

| Raman shift (cm$^{-1}$) | Relative Intensity |
|---|---|
| 13 | strong |
| 24 | strong |
| 34 | medium |
| 67 | strong |
| 77 | strong |
| 208 | weak |
| 283 | weak |
| 348 | weak |
| 422 | medium |
| 495 | weak |
| 552 | weak |

The $^{13}$C solid-state nuclear magnetic resonance (ssNMR) spectrum of Form A is shown in FIG. 4. The ssNMR peak list is provided in Table 4. Selected peaks (with Δ ppm) are provided in Tables 5 and 6.

TABLE 4

| $^{13}$C NMR chemical shift (ppm) |
|---|
| 179.7 |
| 177.9 |
| 177.5 |
| 177.2 |
| 177.0 |
| 165.3 |
| 164.9 |
| 164.8 |
| 67.8 |
| 67.4 |
| 58.6 |
| 58.2 |
| 46.8 |
| 40.3 |
| 33.3 |
| 25.3 |
| 23.5 |
| 21.1 |

TABLE 5

| $^{13}$C NMR chemical shift (ppm) | Δ (ppm) from the most downfield peak at 179.7 ppm |
|---|---|
| 179.7 | 0.0 |
| 177.9 | 1.8 |
| 165.3 | 14.4 |
| 164.9 | 14.8 |
| 164.8 | 14.9 |

TABLE 6

| $^{13}$C NMR chemical shift (ppm) | Δ (ppm) from the most downfield peak at 179.7 ppm |
|---|---|
| 179.7 | 0 |
| 177.9 | 1.8 |
| 40.3 | 139.4 |
| 33.3 | 146.4 |
| 25.3 | 154.4 |
| 23.5 | 156.2 |
| 21.1 | 158.6 |

Form A melts with an onset temperature of 71.71° C. and a peak temperature of 72.06° C. based on DSC analysis. See FIG. 5.

The infrared (IR) spectrum of Form A is shown in FIG. 6. The IR peak list (±4 cm$^{-1}$) is provided in Table 7.

TABLE 7

| Peak Position (cm$^{-1}$) | Relative Intensity |
|---|---|
| 3560 | weak |
| 3400 | medium, broad |
| 3343 | medium |
| 3296 | medium |
| 2881-3012 | medium |
| 1678 | medium |
| 1636 | strong |
| 1589 | medium |
| 1525 | strong |
| 1458 | medium |
| 1435 | medium |
| 1413 | medium |
| 1376 | weak |
| 1352 | medium |
| 1292 | weak |
| 1255 | weak |
| 1214 | strong |
| 1196 | strong |
| 1142 | weak |
| 1120 | weak |
| 1015 | weak |
| 964 | weak |
| 924 | weak |
| 898 | weak |
| 827 | weak |
| 843 | weak |
| 777 | weak |
| 649 | strong |
| 599 | medium |
| 576 | medium |
| 551 | medium |
| 502 | medium |
| 426 | strong |

The near-infrared (NIR) spectrum of Form A is shown in FIG. 7 The NIR peak list (±4 cm$^{-1}$) is provided in Table 8.

TABLE 8

| Peak Position (cm$^{-1}$) | Relative Intensity |
|---|---|
| 5908 | medium |
| 5796 | medium |
| 5145 | strong |
| 4875 | medium |
| 4630 | strong |
| 4423 | strong |
| 4298 | weak |

Figure 9:
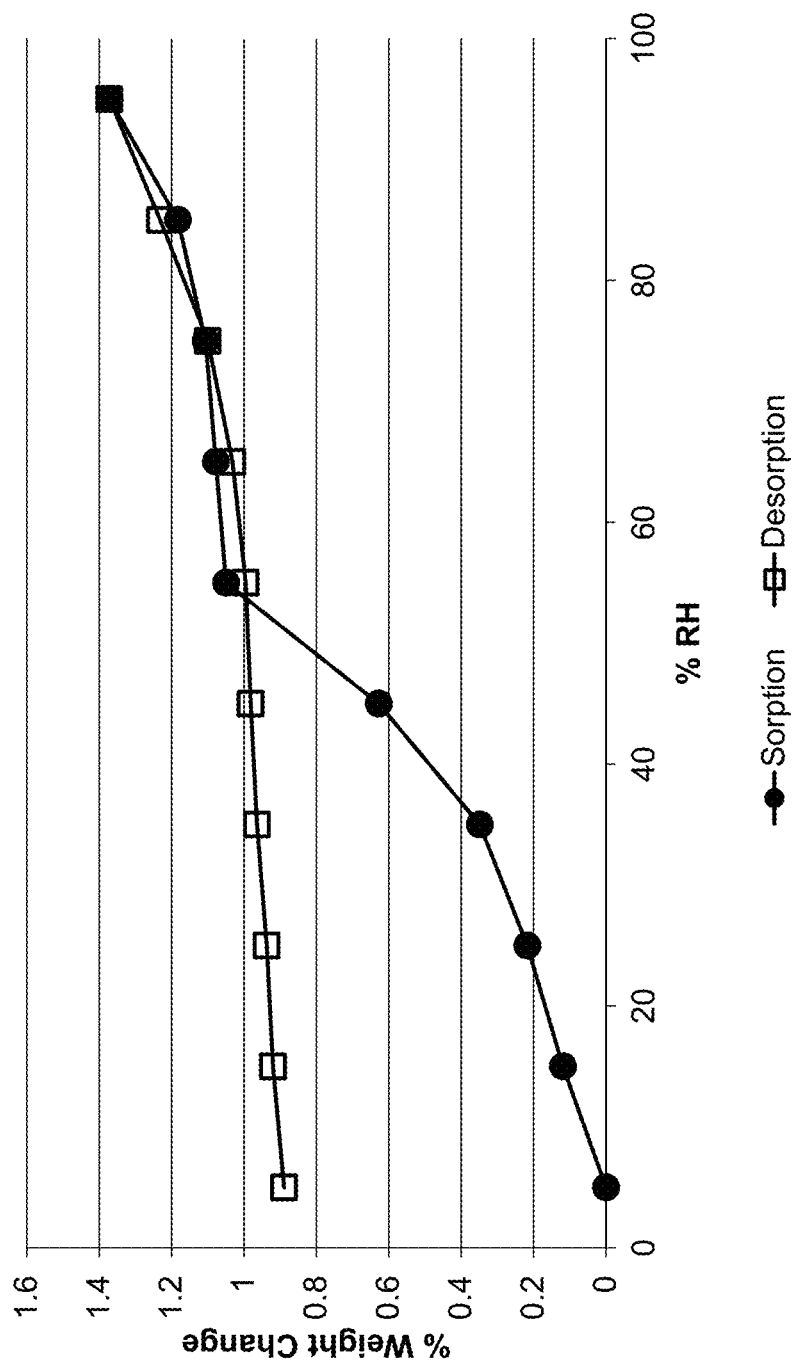
FIG. 9 is a line graph showing the dynamic vapor sorption/desorption data of Form A.
Figure 10:
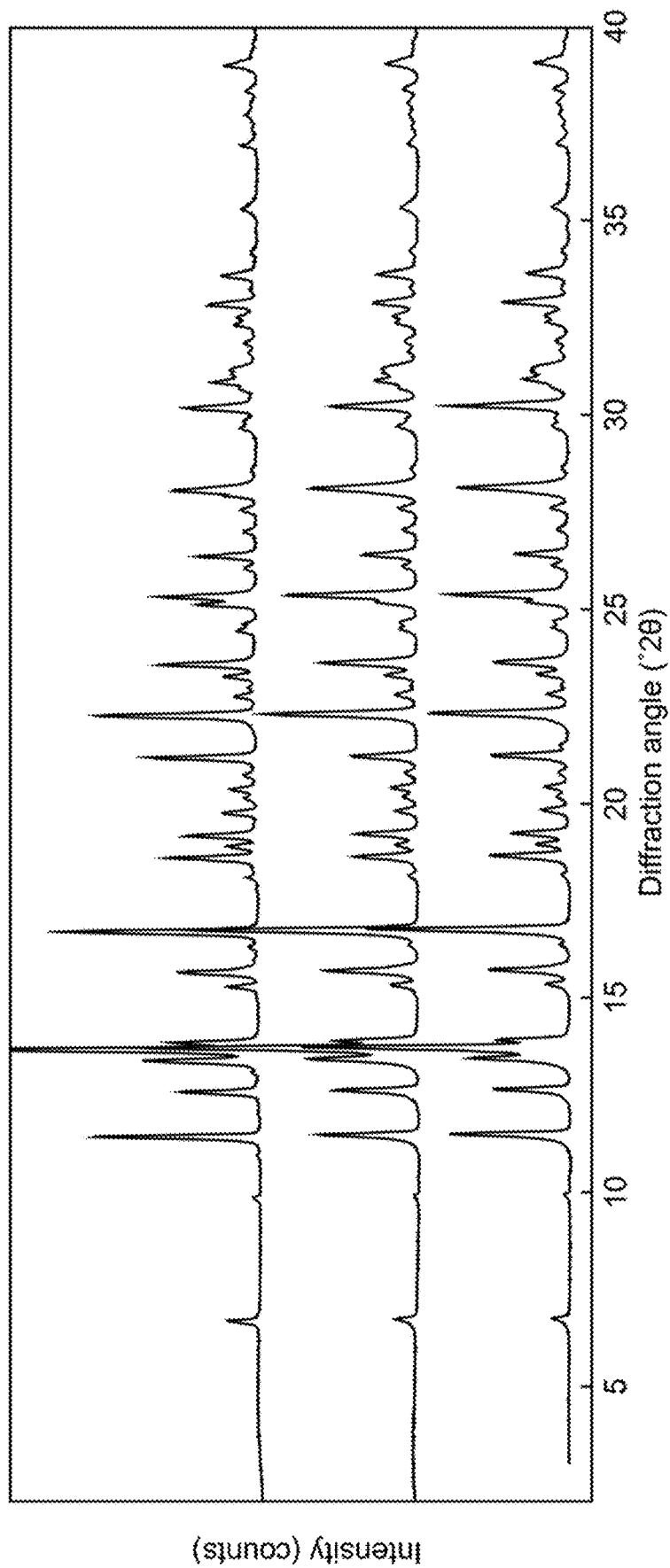
FIG. 10 is a series of three XRPD diffractograms of Form A containing different amounts of water.

Form A is non-hygroscopic. Dynamic vapor sorption-desorption (DVS) analysis of Form A showed little moisture uptake when the material was exposed from 5% RH to 95% RH, and little moisture loss when the material was exposed from 95% RH to 5% RH (FIG. 9). The resulting material after DVS remained as trofinetide Form A by XRPD (FIG. 10).

Figure 12:
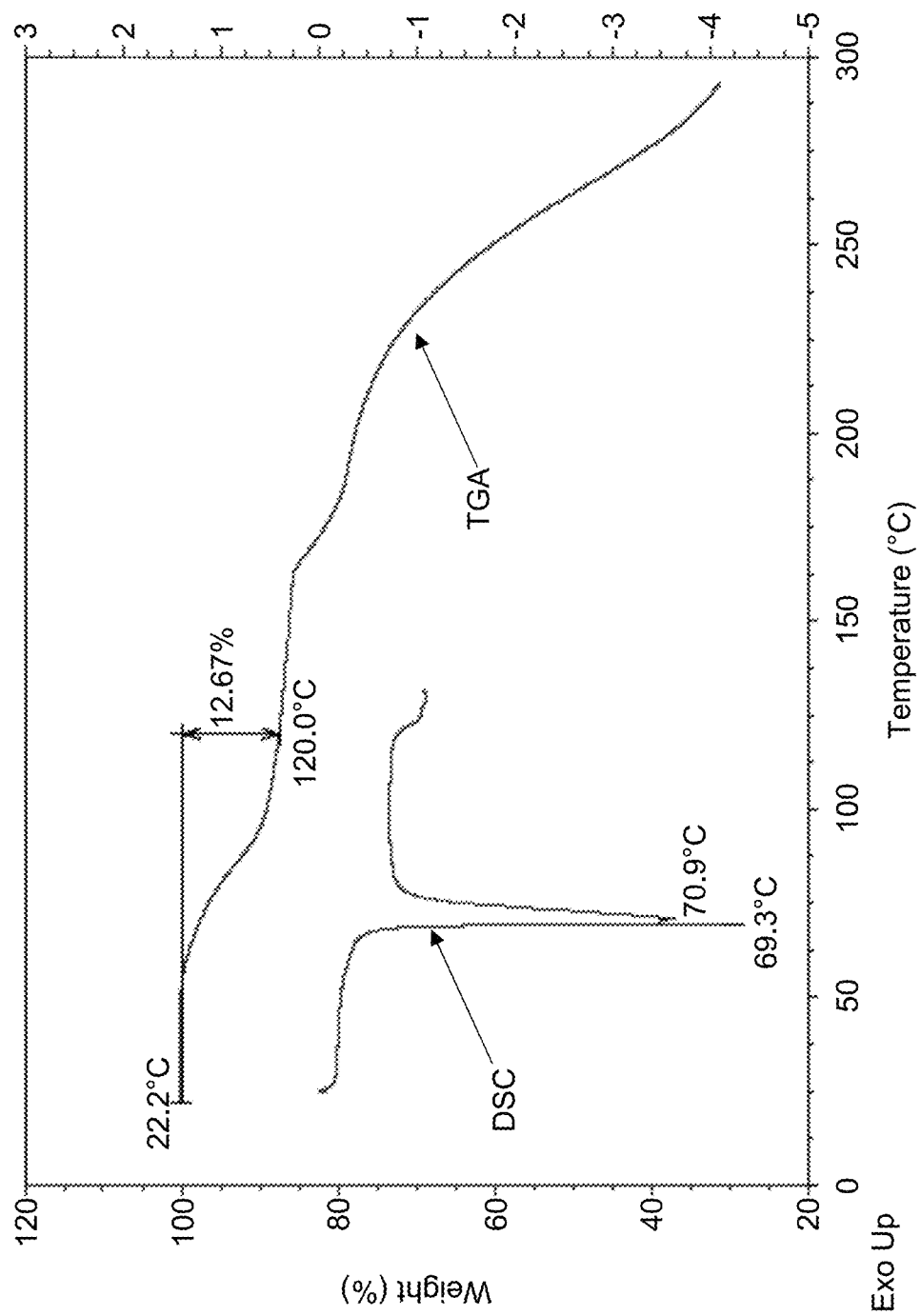
FIG. 12 is a TGA/DCS thermogram of Form A.

Form A exhibits a weight loss of 12-14% between about 50 and 120° C. This is likely due to loss of water and matches the 12-14% water content as measured by Karl Fisher analysis. An example TGA scan is presented in FIG. 12. DSC data for Form A consistently shows a sharp endotherm at about 70-72° C. (peak temperature) that corresponds to melting.

Form A is a trihydrate based on the single crystal X-ray structure that showed three water molecules per molecule of trofinetide (FIG. 8). But Form A has been generated with water content varying from about 12% to about 14%. This suggests that while some of the water is integral to the crystal lattice, at least one of the water molecules may be loosely bound and can be removed without changing the crystal lattice. For this reason, Form A is designated as trofinetide.xH$_2$O, wherein x is about 2 to about 4.

Example 2

Stability of Form A

Figure 11:
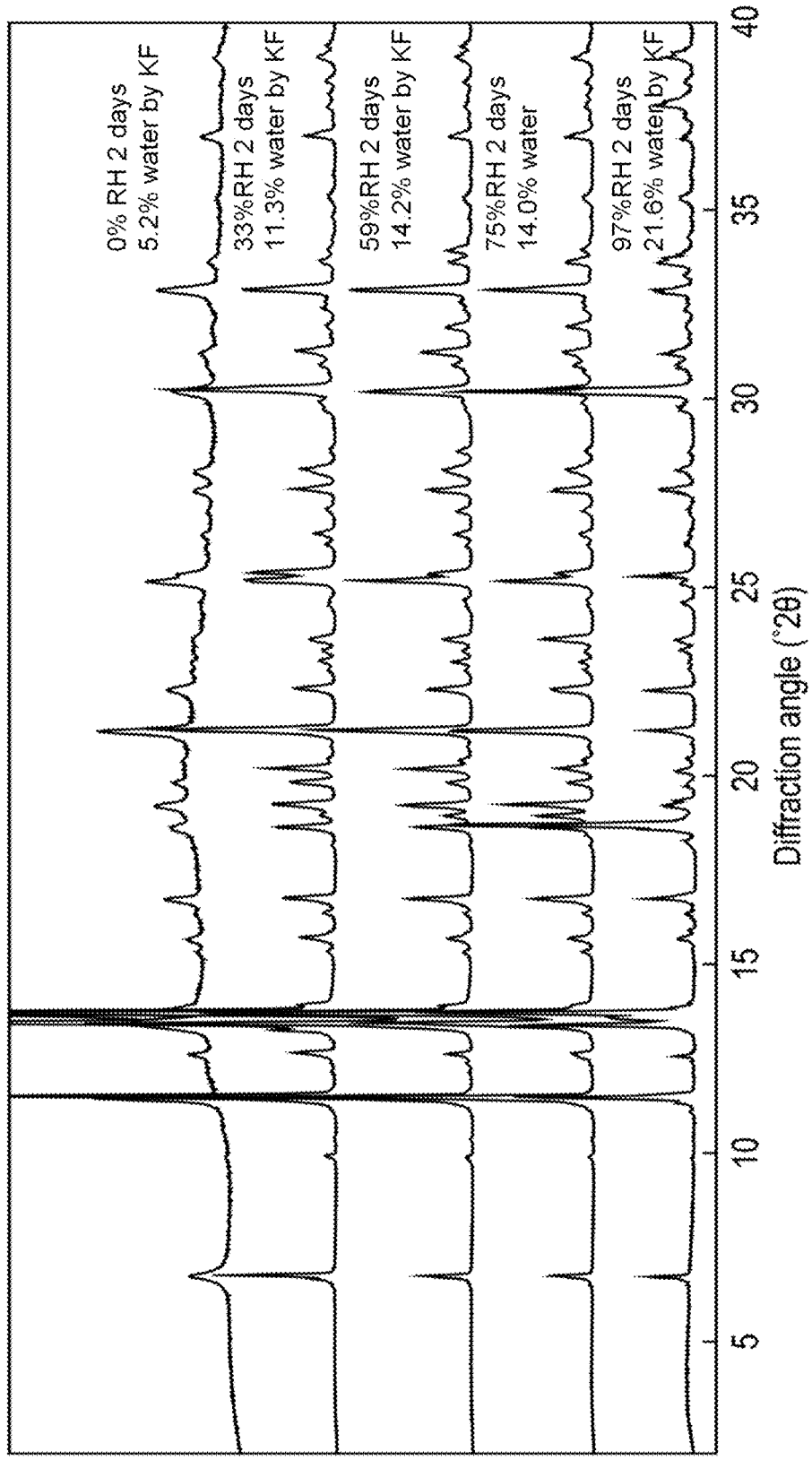
FIG. 11 is a series of five XRPD diffractograms of Form A stored at different humidity conditions.

Form A is stable under a large range of humidity conditions. Form A exposed at 33% RH, 59% RH, 75% RH, and 97% RH for two days showed between 2 and 4 mole equivalents of water. Under extreme dry conditions (open container exposed under 0% RH for two days), Form A lost the water and became disordered. Form A signals are still visible in the XRPD pattern, but the crystalline signals are broad and the XRPD pattern showed some amorphous halo in the baseline indicating formation of disorder and amorphous material (FIG. 11).

The long-term (6 month) chemical stability of Form A and amorphous trofinetide were tested under the same conditions: 25±2° C./60±5% relative humidity (RH). Form A is surprisingly more stable than amorphous trofinetide under these conditions (Table 9).

TABLE 9

| Drug Substance | Total Impurities (25 ± 2° C./60 ± 5% RH) | | | |
|---|---|---|---|---|
| | Initial | 1 month | 3 months | 6 months |
| amorphous trofinetide (Batch 1) | 0.3% | 0.3% | 0.8% | 1.0% |
| amorphous trofinetide (Batch 2) | 0.2% | NT | 0.6% | 0.9% |
| amorphous trofinetide (Batch 3) | 0.2% | 0.2% | 0.6% | 0.8% |
| Form A | <PLOQ | 0.0% | 0.03% | <PLOQ |

PLOQ = Pooled Limit of Quantification;
NT = Not Tested;
RH = Relative Humidity

The analytical method used in the impurity assay is provided in Table 10.

TABLE 10

| Parameter | Settings | | |
|---|---|---|---|
| HPLC column | Waters Acquity CSH C18, 1.7 μm, 150 × 2.1 mm | | |
| Mobile Phase A | 0.1% TFA/Water (v/v) | | |
| Mobile Phase B | 0.1% TFA in 30% Acetonitrile/70% Water (v/v/v) | | |
| Blank/Diluent | Water | | |
| Gradient | Time (min) | % A | % B |
| | 0 | 94 | 6 |
| | 22 | 72 | 28 |
| | 40 | 0 | 100 |
| | 40.1 | 94 | 6 |
| | 50 | 94 | 6 |
| Flow rate | 0.35 mL/min | | |
| Autosampler temperature | 4° C. | | |
| Column oven temperature | 40° C. | | |
| Injection volume | 4 μL | | |
| Detection | 220 nm | | |
| Assay Standard and Sample Solution Concentrations | Resolution and ID Standard - Assay Sample and Standards - | 0.5 mg/mL trofinetide in diluent 0.5 mg/mL trofinetide in diluent | |
| Impurities Standard and Sample Solution Concentrations | Resolution and ID Standard - Standard Solution - Impurity Sample - | 0.5 mg/mL trofinetide in diluent 0.5 mg/mL trofinetide in diluent 1 mg/mL trofinetide in diluent | |

It is to be understood that the foregoing described embodiments and exemplifications are not intended to be limiting in any respect to the scope of the disclosure, and that the claims presented herein are intended to encompass all embodiments and exemplifications whether or not explicitly presented herein.

All patents and publications cited herein are fully incorporated by reference in their entirety.

What is claimed is:

1. Crystalline trofinetide.xH$_2$O, wherein x is about 2 to about 4, characterized as having:
   (i) a powder x-ray diffraction pattern with a peak in the range of 6.6-6.8, a peak in the range of 11.3-11.6, a peak in the range of 12.5-12.7, and a peak in the range of 13.6-13.8 degrees 2Θ using Cu Kα radiation, wherein the 2Θ values are ±0.2 degrees 2Θ; or
   (ii) a powder x-ray diffraction pattern with d-spacings at 13.1, 7.7, 7.0, 6.4, and 5.3 Å using Cu Kα radiation; or
   (iii) a FT-Raman spectrum with peaks at 2989, 2934, 2883, 1685, 1637, 1459, and 930 cm-1, wherein the cm-1 values are ±4 cm-1; or
   (iv) a low frequency (LF) Raman spectrum with peaks at 13, 24, 67, and 77 cm-1, wherein the cm-1 values are ±4 cm-1; or
   (v) a 13C solid-state nuclear magnetic resonance spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 pm; or
   (vi) a 13C solid-state nuclear magnetic resonance spectrum with 18 peaks, wherein the Δ from the furthest downfield peak to: (i) the second furthest downfield peak is 1.8 ppm; (ii) the third furthest downfield peak is 2.2 ppm; (iii) the fourth furthest downfield peak is 2.5 ppm; (iv) the fifth furthest downfield peak is 2.7 ppm; (v) the sixth furthest downfield peak is 14.4 ppm; (vi) the seventh furthest downfield peak is 14.8 ppm; (vii) the eighth furthest downfield peak is 14.9 ppm; (viii) the ninth furthest downfield peak is 111.9 ppm; (ix) the tenth furthest downfield peak is 112.3 ppm; (x) the eleventh furthest downfield peak is 121.1 ppm; (xi) the twelfth furthest downfield peak is 121.5 ppm; (xii) the thirteenth furthest downfield peak is 133.1 ppm; (xiii) the fourteenth furthest downfield peak is 139.4 ppm; (xiv) the fifteenth furthest downfield peak is 146.3 ppm; (xv) the sixteenth furthest downfield peak is 154.6 ppm; (xvi) the seventeenth furthest downfield peak is 156.2 ppm; and/or (xvii) the Δ from the furthest downfield peak to the furthest upfield peak is 158.6 ppm, or any combination thereof; or
   (vii) a melting point with an onset temperature of 71.71° C. and a peak temperature of 72.06° C. based on differential scanning calorimetry; or
   (viii) an infrared (IR) spectrum with peaks at 1678, 1636, 1589, 1525, 1214, and 1196 cm-1, wherein the cm-1 values are ±4 cm-1; or (ix) a near-infrared (NIR) spectrum with peaks at 5145, 4630, and 4423 cm-1, wherein the cm-1 values are ±4 cm-1; or a combination thereof.

2. The crystalline trofinetide.xH$_2$O of claim 1, characterized as having a powder x-ray diffraction pattern with peaks at 6.7 or 6.8, 11.4 or 11.5, 12.6, and 13.7 or 13.8 degrees 2Θ using Cu Kα radiation, wherein the 2Θ values are ±0.2 degrees 2Θ.

3. The crystalline trofinetide.xH$_2$O of claim 2, characterized as having a powder x-ray diffraction pattern with peaks at 6.7, 11.4, 12.6, 13.7, 22.3, 23.6, 25.3 and 28.1 degrees 2Θ using Cu Kα radiation, wherein the 2Θ values are ±0.2 degrees 2Θ.

4. The crystalline trofinetide.xH$_2$O of claim 1, characterized as having a powder x-ray diffraction pattern with d-spacings at 13.1, 7.7, 7.0, 6.4, and 5.3 Å using Cu Kα radiation.

5. The crystalline trofinetide.xH$_2$O of claim 1, characterized as having an FT-Raman spectrum with peaks at 2989, 2934, 2883, 1685, 1637, 1459, and 930 cm$^{-1}$, wherein the cm$^{-1}$ values are ±4 cm$^{-1}$.

6. The crystalline trofinetide.xH$_2$O of claim 1, characterized as having a low frequency (LF) Raman spectrum with peaks at 13, 24, 67, and 77 cm$^{-1}$, wherein the cm$^{-1}$ values are ±4 cm$^{-1}$.

7. The crystalline trofinetide.xH$_2$O of claim 1, characterized as having a $^{13}$C solid-state nuclear magnetic resonance spectrum with peaks at 179.7, 177.9, 177.5, 177.2, 177.0, 165.3, 164.9, 164.8, 67.8, 67.4, 58.6, 58.2, 46.8, 40.3, 33.3, 25.3, 23.5, and 21.1 ppm, wherein the ppm values are ±3 pm.

8. The crystalline trofinetide.xH$_2$O of claim 1, characterized as having a melting point with an onset temperature of 71.71° C. and a peak temperature of 72.06° C. based on differential scanning calorimetry.

9. The crystalline trofinetide.xH$_2$O of claim 1, characterized as having an infrared (IR) spectrum with peaks at 1678, 1636, 1589, 1525, 1214, and 1196 cm$^{-1}$, wherein the cm$^{-1}$ values are ±4 cm$^{-1}$.

10. The crystalline trofinetide.xH$_2$O of claim 1, characterized as having a near-infrared (NIR) spectrum with peaks at 5145, 4630, and 4423 cm$^{-1}$, wherein the cm$^{-1}$ values are ±4 cm$^{-1}$.

11. The crystalline trofinetide.xH$_2$O of claim 1, wherein x is about 2.5 to about 3.5.

12. The crystalline trofinetide.xH$_2$O of claim 1, wherein x is about 3.

13. A pharmaceutical composition comprising the crystalline trofinetide.xH$_2$O of claim 1 and a pharmaceutically acceptable excipient.

14. An aqueous pharmaceutical formulation comprising the crystalline trofinetide.xH$_2$O of claim 1 dissolved in water.

15. A method of making the aqueous pharmaceutical formulation of claim 1, the method comprising admixing the crystalline trofinetide.xH$_2$O and water.

16. A kit comprising the crystalline trofinetide.xH$_2$O of claim 1 and instructions for dissolving crystalline trofinetide.xH$_2$O in a water to provide an aqueous pharmaceutical formulation.

17. A method of treating a disease, disorder or condition in a subject in need thereof, the method comprising administering the pharmaceutical composition of claim 13 to the subject, wherein the disease, disorder or condition is traumatic brain injury, neurodevelopmental disorder, Rett Syndrome, Fragile X Syndrome, or autism spectrum disorder.

18. The method of claim 17, wherein the disease, disorder or condition is Rett Syndrome.

19. A method of making the crystalline trofinetide.xH$_2$O of claim 1, the method comprising i) adding ethanol to an aqueous solution of trofinetide at about 25° C.; ii) cooling the solution to about 0° C.; and iii) isolating the solid thus obtained to give crystalline trofinetide.xH$_2$O.

* * * * *